United States Patent
Murphy et al.

(10) Patent No.: US 11,628,227 B2
(45) Date of Patent: Apr. 18, 2023

(54) MINERAL COATED MICROPARTICLES FOR GENE DELIVERY IN CHRONIC WOUND THERAPY

(71) Applicant: Wisconsin Alumni Research Foundation, Madison, WI (US)

(72) Inventors: William L. Murphy, Waunakee, WI (US); Andrew Salim Khalil, Madison, WI (US); Xiaohua Yu, Mansfield Center, CT (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/626,971

(22) PCT Filed: Jul. 5, 2018

(86) PCT No.: PCT/US2018/040918
§ 371 (c)(1),
(2) Date: Dec. 27, 2019

(87) PCT Pub. No.: WO2019/010304
PCT Pub. Date: Jan. 10, 2019

(65) Prior Publication Data
US 2020/0138976 A1 May 7, 2020

Related U.S. Application Data

(60) Provisional application No. 62/528,575, filed on Jul. 5, 2017.

(51) Int. Cl.
*A61K 48/00* (2006.01)
*A61K 9/50* (2006.01)

(52) U.S. Cl.
CPC .......... *A61K 48/0033* (2013.01); *A61K 9/501* (2013.01); *A61K 9/5078* (2013.01)

(58) Field of Classification Search
None
See application file for complete search history.

(56) References Cited

U.S. PATENT DOCUMENTS

2009/0074850 A1\* 3/2009 Pupo Escalona ....... A61P 17/00
424/450
2009/0286852 A1\* 11/2009 Kariko ................. A61K 48/005
514/44 R (Continued)

FOREIGN PATENT DOCUMENTS

EP 1151966 A1 11/2001
WO 2010036919 A1 1/2010

(Continued)

OTHER PUBLICATIONS

HS Kim, HS Yoo. "In vitro and in vivo epidermal growth factor gene therapy for diabetic ulcers with electrospun fibrous meshes." Acta Biomaterialia, vol. 9, 2013, pp. 7371-7380. (Year: 2013).\*

(Continued)

*Primary Examiner* — Isaac Shomer
(74) *Attorney, Agent, or Firm* — Stinson LLP

(57) ABSTRACT

Disclosed are formulations for providing a therapeutic bioactive polypeptide to injured tissue. Formulations include mineral coated microparticles wherein a polynucleotide is adsorbed to the mineral layer. Other formulations include a carrier including mineral coated microparticles wherein mineral coated microparticles include a polynucleotide. Also disclosed are methods for sustained delivery of a bioactive polypeptide and methods for treating chronic wounds using a formulation for providing sustained delivery of the bioactive peptide.

10 Claims, 21 Drawing Sheets

(56) References Cited

U.S. PATENT DOCUMENTS

| | | | |
|---|---|---|---|
| 2011/0305760 A1 | 12/2011 | Murphy et al. | |
| 2013/0259924 A1* | 10/2013 | Bancel | A61K 48/0066 424/450 |
| 2014/0161886 A1* | 6/2014 | Murphy | A61K 9/501 424/490 |
| 2015/0238655 A1* | 8/2015 | Jongpaiboonkit | A61K 38/1875 424/423 |
| 2016/0017368 A1* | 1/2016 | Murphy | C12N 15/85 506/14 |

FOREIGN PATENT DOCUMENTS

| | | | |
|---|---|---|---|
| WO | 2016017368 A1 | 4/2016 | |
| WO | 2016141242 A1 | 9/2016 | |
| WO | WO-2017214175 A1 * | 12/2017 | A61K 31/7115 |

OTHER PUBLICATIONS

W Xiao, H Fu, MN Rahaman, Y Liu, BS Bal. "Hollow hydroxyapatite microspheres: A novel bioactive and osteoconductive carrier for controlled release of bone morphogenetic protein-2 in bone regeneration." Acta Biomaterialia, vol. 9, 2013, pp. 8374-8383. (Year: 2013).*

P Parikh et al. "Regeneration of axons in injured spinal cord by activation of bone morphogenetic protein/Smad1 signaling pathway in adult neurons." Proceedings of the National Academy of Sciences, vol. 108, No. 19, May 10, 2011, pp. E99-E107. (Year: 2011).*

L Jongpaiboonkit, T Franklin-Ford, WL Murphy. "Mineral-Coated Polymer Microspheres for Controlled Protein Binding and Release." Advanced Materials, vol. 21, 2009, pp. 1960-1963. (Year: 2009).*

J Baek, H-D Jung, T-S Jang, SW Kim, M-H Kang, H-E Kim, Y-H Koh. "Synthesis and evaluation of bone morphogenetic protein (BMP)-loaded hydroxyapatite microspheres for enhanced bone regeneration." Ceramics International, vol. 42, 2016, pp. 7748-7756, available online Feb. 1, 2016. (Year: 2016).*

I Ono, T Yamashita, H-Y Jin, Y Ito, H Hamada, Y Akasaka, M Nakasu, T Ogawa, K Jimbow. "Combination of porous hydroxyapatite and cationic liposomes as a vector for BMP-2 gene therapy." Biomaterials, vol. 25, 2004, pp. 4709-4718. (Year: 2004).*

B Storek, M Reinhardt, C Wang, WGM Janssen, NM Harder, MS Banck, JH Morrison, AS Beutler. "Regeneration of axons in injured spinal cord by activation of bone morphogenetic protein/Smad1 signaling pathway in adult neurons." PNAS, vol. 108 No. 19, May 10, 2011, pp. E99-E107. (Year: 2011).*

MJ Kwon et al. "Effective healing of diabetic skin wounds by using nonviral gene therapy based on minicircle vascular endothelial growth factor DNA and a cationic dendrimer." The Journal of Gene Medicine, vol. 14, 2012, pp. 272-278. (Year: 2012).*

Derek Lowe. "Spike Protein Behavior." In the Pipeline, https://www.science.org/content/blog-post/spike-protein-behavior accessed Dec. 13, 2021, originally published May 4, 2021, pp. 1-13. (Year: 2021).*

Kizzmekia S. Corbett et al. "SARS-CoV-2 mRNA vaccine design enabled by prototype pathogen preparedness." Nature, vol. 586, Oct. 22, 2020, pp. 567-571. (Year: 2020).*

David L. Steed, MD, and the Diabetic Ulcer Study Group. "Clinical evaluation of recombinant human platelet-derived growth factor for the treatment of lower extremity diabetic ulcers." Journal of Vascular Surgery, vol. 21, 1995, pp. 71-81. (Year: 1995).*

Robert Blakytny et al. "Lack of insulin-like growth factor 1 (IGF1) in the basal keratinocyte layer of diabetic skin and diabetic foot ulcers." Journal of Pathology, vol. 190, 2000, pp. 589-594. (Year: 2000).*

Hong et al., Composites of poly(lactide-co-glycolide) and the surface modified carbonated hydroxyapatite nanoparticles, Journal of Biomedical Materials Research Part A, DOI 10.1102/jbm.a, 2006, pp. 515-522.

Kawai et al., Accelerated wound healing through the incorporation of basic fibroblast growth factor-impregnated gelatin microspheres into artificial dermis using a pressure-induced decubitus ulcer model in genetically diabetic mice, British Journal of Plastic Surgery, 2005, 58, pp. 1115-1123.

Yu et al., Nanostructured Mineral Coatings Stablize Proteins for Therapeutic Delivery, Adv Mater. Sep. 2017, 29(33) pp. 1-18.

* cited by examiner

[scale bar=2μm]

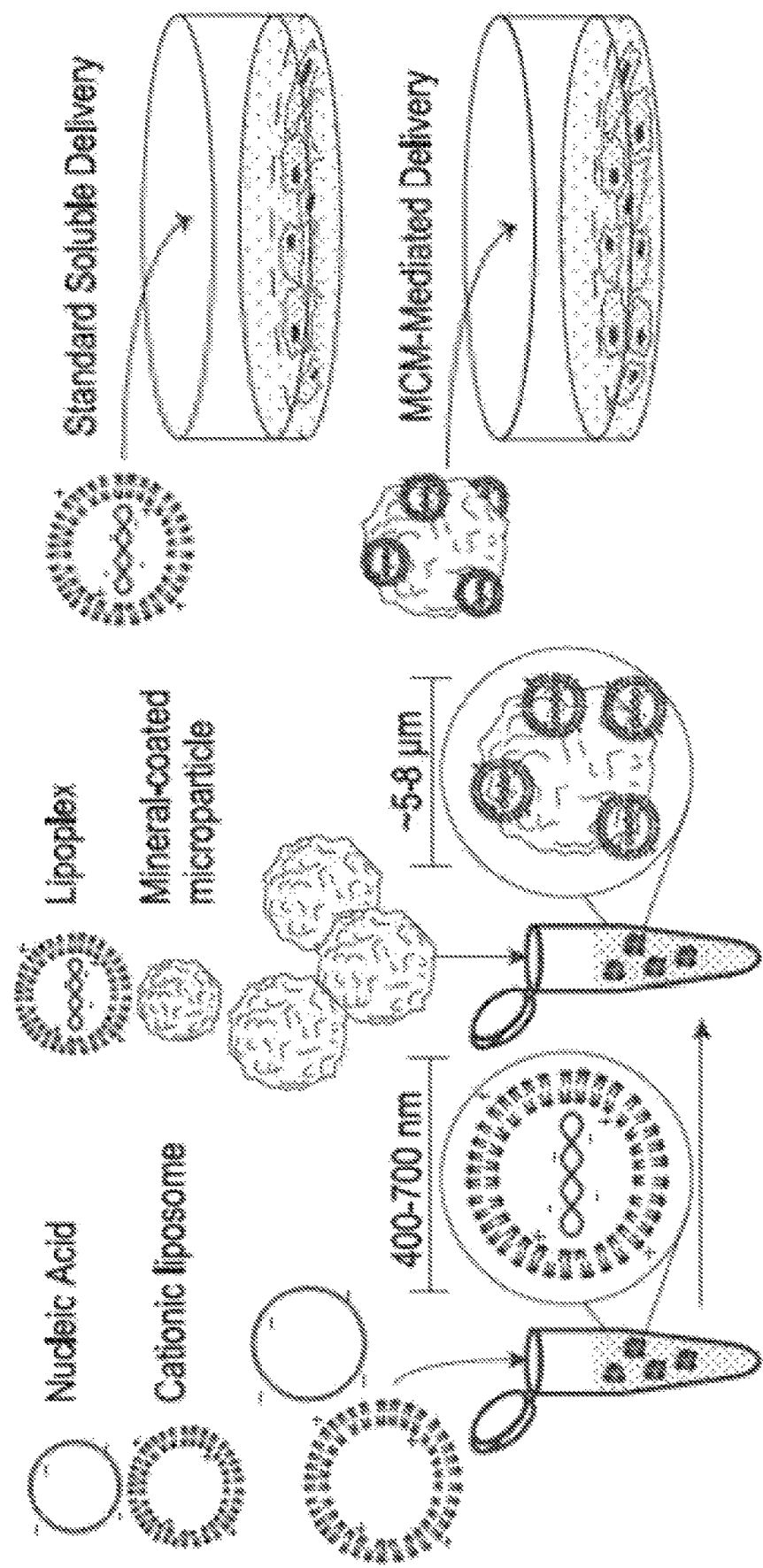

[scale bar=500μm]

[scale bar=500μm]

[scale bar=500μm]

*p-value ≤ 0.05

48 hrs post-transfection

US 11,628,227 B2

MINERAL COATED MICROPARTICLES FOR GENE DELIVERY IN CHRONIC WOUND THERAPY

CROSS-REFERENCE TO RELATED APPLICATIONS

This application claims priority to International Patent Application No. PCT/US2018/040918, filed Jul. 5, 2018, which claims priority to U.S. Provisional Application No. 62/528,575 filed Jul. 5, 2017, both of which are hereby incorporated by reference in their entireties.

STATEMENT REGARDING FEDERALLY SPONSORED RESEARCH OR DEVELOPMENT

This invention was made with government support under RD-83573701-0 awarded by the Environmental Protection Agency and 1256259 awarded by the National Science Foundation. The government has certain rights in the invention.

BACKGROUND

The present disclosure is directed to mineral coated microparticles (MCMs) and methods of their use for non-viral gene delivery. Particularly, the MCMs provide for non-viral delivery of polynucleotides (e.g., messenger RNA encoding therapeutically relevant released bioactive polypeptides (e.g., cytokines, growth factors). Moreover, the MCMs provide a multi-functional platform that allows for the delivery of polynucleotides, translation to the bioactive polypeptide of interest, and sequestration of the polypeptide for sustained activity/delivery. The MCMs can be used for treating chronic wounds.

Gene delivery is a fundamental strategy to regulate gene expression across therapeutic and research applications in regenerative medicine. Classic non-viral gene delivery strategies utilize plasmid DNA (pDNA) to deliver the gene of interest. However, these methods are not ideal for in vivo application due to risks of insertional mutagenesis and low nuclear transfer efficiency of pDNA to non-mitotic populations.

Relative to pDNA strategies, non-viral delivery of messenger RNA (mRNA) is safe and achieves high transfection efficiency in non-mitotic cells. Unfortunately, this approach is often limited by short-lived time frames of desired gene upregulation—on the order of hours.

Based on prior work using mineral-coat microparticles (MCMs) for both non-viral transfection and sustained delivery of recombinant growth factors, it was hypothesized that MCMs could be leveraged to improve the biological response in mRNA delivery strategies by sequestering and stably releasing an overexpressed bioactive polypeptide (e.g., cytokine, growth factor), thereby extending its biological effects.

Based on the foregoing, MCMs have been designed for both efficient non-viral transfection and stable protein delivery to provide an improved non-viral delivery strategy of bioactive polypeptides such as basic fibroblast growth factor-encoding mRNA (bFGF-mRNA). These MCMs can be used to provide improved tissue repair in subjects, such as in subjects suffering from chronic wounds.

BRIEF DESCRIPTION

The present disclosure is generally directed to mineral coated microparticles (MCMs) including a mineral layer and a polynucleotide and uses thereof. In one embodiment, the polynucleotide is adsorbed to the mineral layer coating the MCMs. In one embodiment, the polynucleotide is condensed to form a polynucleotide complex, which is then adsorbed to the mineral layer. In one embodiment, the polynucleotide is incorporated within the mineral layer. In one embodiment, the polynucleotide is both adsorbed to the mineral layer and incorporated within the mineral layer.

The MCMs can advantageously facilitate efficient non-viral gene delivery in vitro and in vivo while reducing the cytotoxicity associated with common transfection reagents. In addition, the mineral layer(s) of the MCMs serves to sequester and stably release overexpressed released bioactive polypeptide (e.g., cytokine, growth factor) after gene delivery and thereby extends the biological effects of the released cytokine or growth factor.

Accordingly, in one aspect, the present disclosure is directed to a method of repairing injured tissue in a subject in need thereof, the method comprising: contacting a microparticle comprising a mineral layer with a polynucleotide, wherein the polynucleotide is adsorbed to the mineral layer; and contacting the mineral layer with the injured tissue.

In another aspect, the present disclosure is directed to a method for sustained delivery of bioactive polypeptides, the method comprising: contacting a mineral coated microparticle comprising a mineral layer with a polynucleotide adsorbed thereto with at least one cell, wherein, as the coating of the mineral coated microparticle degrades, the microparticle releases a bioactive polypeptide encoded by the polynucleotide to the cell; and sequestering the bioactive polypeptide by the mineral coated microparticle.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A is a schematic of a MCM-mediated nucleic acid delivery strategy.

DETAILED DESCRIPTION

Figure 1A:
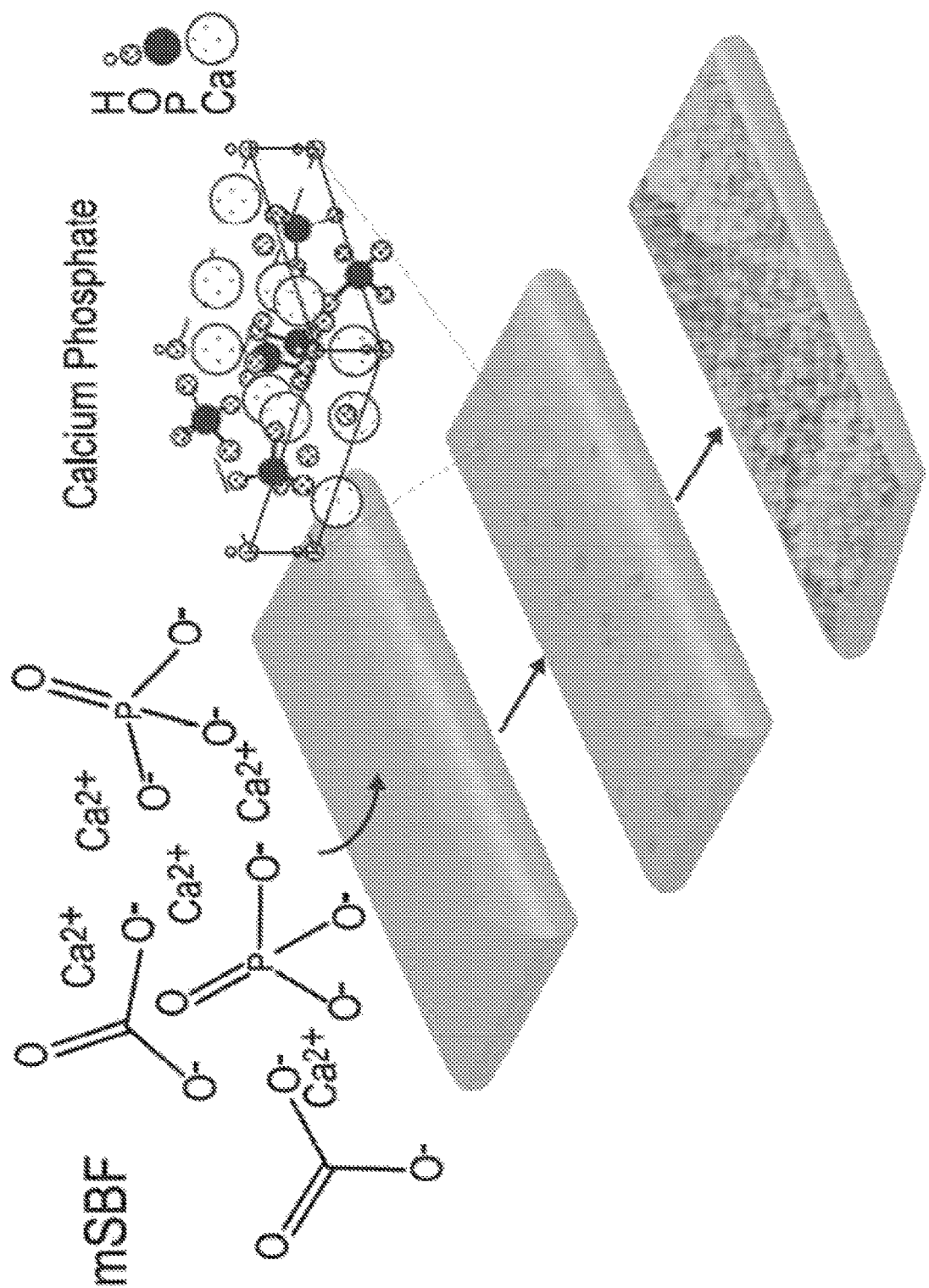
FIG. 1A is a general schematic of a mineral layer coating a surface such as a microparticle formed via biomimetic nucleation and growth in modified simulated body fluid (mSBF) with the addition of sodium fluoride.

The present disclosure is directed to the use of mineral coated microparticles (MCMs) wherein a polynucleotide is adsorbed to the mineral layer coating the microparticle. In some embodiments, the polynucleotide is condensed to form a polynucleotide lipid, polymer or mineral complex, which is then adsorbed to the mineral layer. Also disclosed are methods for sustained delivery of polynucleotides and their released bioactive polypeptides (e.g., cytokines, growth factors), and methods for treating chronic wounds and other injuries in need of tissue repair using MCMs for facilitating efficient non-viral gene delivery. As used herein, "polypeptides" refer to polypeptides and peptides. Additionally, the mineral layer serves to sequester and stably release the overexpressed released bioactive polypeptides after gene delivery, thereby extending their biological effects.

Methods of Tissue Repair

In one aspect, the present disclosure is generally directed to a method of repairing injured tissues in a subject in need thereof. The methods generally include contacting a microparticle having a mineral layer with a polynucleotide and contacting the mineral coated microparticle with the injured tissue.

The microparticle may include any suitable material as the core substrate upon which the mineral layer is formed. Particularly suitable core materials on which the mineral layer is formed include polymers, ceramics, metals, glass and combinations thereof in the form of particles. Suitable particles can be, for example, agarose beads, latex beads, magnetic beads, polymer beads, ceramic beads, metal beads (including magnetic metal beads), glass beads and combinations thereof. The microparticle includes ceramics (e.g., hydroxyapatite, beta-tricalcium phosphate (beta-TCP, β-TCP), magnetite, neodymium), plastics (e.g., polystyrene, poly-caprolactone), hydrogels (e.g., polyethylene glycol; poly(lactic-co-glycolic acid), and the like, and combinations thereof. Particularly suitable core materials are those that dissolve in vivo such as, for example, beta-tricalcium phosphate (beta-TCP, β-TCP) and/or hydroxyapatite (HAP).

The core substrates can initially be coated with a poly(α-hydroxy ester) film, for example. Particularly suitable poly (α-hydroxy esters) may be, for example, poly(L-lactide), poly(lactide-co-glycolide), poly(ε-caprolactone), and combinations thereof. It should be understood that when making any combinations of the above films, the films are typically mixed in suitable organic solvents as known in the art. Further, differences in molecular weights, crystallization rates, glass transition temperatures, viscosities, and the like should be taken into consideration as well as understood in the art to prevent phase separation and lack of uniformity in the final substrates. Phase separation and lack of uniformity can further be avoided by altering the mixing ratio of the films used in the substrate.

After preparing a poly(α-hydroxy ester) film on the substrate, the surface of the film coating is hydrolyzed under alkaline conditions to create a surface having COOH and OH groups. After surface hydrolyzing, the substrate is incubated in a simulated body fluid containing a suitable mineral-forming material to form a mineral layer. Suitable mineral-forming materials may be, for example, calcium, phosphate, carbonate, and combinations thereof.

To prepare a mineral coated microparticle (MCM), a core material is incubated in a modified simulated body fluid. The modified simulated body fluid includes calcium and phosphate, which form the mineral layer on the surface of the core, which results in the MCM. Different mineral layer morphologies can be achieved by varying the amounts and ratios of calcium, phosphate, and carbonate. Different mineral layer morphologies include, for example, plate-like structures and spherulite-like structures. High carbonate concentration results in a mineral layer having a plate-like structure. Low carbonate concentration results in a mineral layer having a spherulite-like structure. The mineral layer morphology also affects adsorption of the polynucleotide.

The simulated body fluid (SBF) for use in preparing the mineral coated microparticles typically includes from about 5 mM to about 12.5 mM calcium ions, including from about 7 mM to about 10 mM calcium ions, and including about 8.75 mM calcium ions; from about 2 mM to about 12.5 mM phosphate ions, including from about 2.5 mM to about 7 mM phosphate ions, and including from about 3.5 mM to about 5 mM phosphate ions; and from about 4 mM to about 100 mM carbonate ions.

In some embodiments, the SBF can further include about 145 mM sodium ions; from about 6 mM to about 9 mM potassium ions; about 1.5 mM magnesium ions; from about 150 mM to about 175 mM chloride ions; about 4 mM $HCO_3^-$; and about 0.5 mM $SO_4^{2-}$ ions.

The pH of the SBF can typically range from about 4 to about 7.5, including from about 5.3 to about 6.8, including from about 5.7 to about 6.2, and including from about 5.8 to about 6.1.

Suitable SBF can include, for example: about 145 mM sodium ions; about 6 mM to about 9 mM potassium ions; about 5 mM to about 12.5 mM calcium ions; about 1.5 mM magnesium ions; about 150 mM to about 175 mM chloride ions; about 4.2 mM $HCO_3$; about 2 mM to about 5 mM $HPO_4^{2-}$ ions; and about 0.5 mM $SO_4^{2-}$ ions. The pH of the simulated body fluid may be from about 5.3 to about 7.5, including from about 6 to about 6.8.

In one embodiment, the SBF may include, for example: about 145 mM sodium ions; about 6 mM to about 17 mM potassium ions; about 5 mM to about 12.5 mM calcium ions; about 1.5 mM magnesium ions; about 150 mM to about 175 mM chloride ions; about 4.2 mM to about 100 mM $HCO_3$; about 2 mM to about 12.5 mM phosphate ions; and about 0.5 mM $SO_4^{2-}$ ions. The pH of the simulated body fluid may be from about 5.3 to about 7.5, including from about 5.3 to about 6.8.

In another embodiment, the SBF includes: about 145 mM sodium ions; about 6 mM to about 9 mM potassium ions; from about 5 mM to about 12.5 mM calcium ions; about 1.5 mM magnesium ions; about 60 mM to about 175 mM chloride ions; about 4.2 mM to about 100 mM $HCO_3$; about 2 mM to about 5 phosphate ions; about 0.5 mM $SO_4^{2-}$ ions; and a pH of from about 5.8 to about 6.8, including from about 6.2 to about 6.8.

In yet another embodiment, the SBF includes: about 145 mM sodium ions; about 9 mM potassium ions; about 12.5 mM calcium ions; about 1.5 mM magnesium ions; about 172 mM chloride ions; about 4.2 mM $HCO_3^-$; about 5 mM to about 12.5 mM phosphate ions; about 0.5 mM $SO_4^{2-}$ ions; from about 4 mM to about 100 mM $CO_3^{2-}$; and a pH of from about 5.3 to about 6.0.

In some embodiments, the mineral layer will further include a dopant. Suitable dopants include halogen ions, for example, fluoride ions, chloride ions, bromide ions, and iodide ions. The dopant(s) can be added with the other components of the SBF prior to incubating the substrate in the SBF to form the mineral coating.

In one embodiment, the halogen ions include fluoride ions. Suitable fluoride ions can be provided by fluoride ion-containing agents such as sodium fluoride.

The fluoride ion-containing agent is generally included in the SBF to provide an amount of up to 100 mM fluoride ions, including from about 0.001 mM to about 100 mM, including from about 0.01 mM to about 50 mM, including from about 0.1 mM to about 15 mM, and including about 1 mM fluoride ions.

It has been found that the inclusion of one or more dopants in the SBF results in the formation of a halogen-doped mineral coating that significantly enhances the efficiency of biomolecule delivery to cells.

Additional mineral layers are formed using SBF including one or more ions and concentrations of ions as shown in Table 1:

TABLE 1

| Mineral ion | Concentration (μM) |
|---|---|
| NaCl | 141.0 |
| KCl | 4.0 |
| $MgCl_2$ | 1.0 |
| $MgSO_4$ | 0.5 |
| $NaHCO_3$ | 4-100 |
| $CaCl_2$ | 2.5-15 |
| $KH_2PO_4$ | 1-5 |
| NaF | 0.1-100 |
| Other Dopants (Ag, Sr, etc.) | varies |

In embodiments that include a mineral layer, the core substrate is incubated in a formulation of modified simulated body fluid. The layer of mineral forms on the core during the incubation period of minutes to days. After the initial layer of mineral is formed on the core, the mineral coated microparticle can be removed from the modified simulated body fluid and washed. To form a plurality of layers of mineral coating a mineral coated microparticle is incubated in a second, third, fourth, etc. modified simulated body fluid until the desired number of layers of mineral coating is achieved. During each incubation period a new layer of mineral coating forms on the previous layer. These steps are repeated until the desired number of layers of mineral coating is achieved.

After completion of the mineral layer preparation, the mineral layers may be analyzed to determine the morphology and composition of the mineral layers. The composition of the mineral layers may be analyzed by energy dispersive X-ray spectroscopy, Fourier transform infrared spectrometry, X-ray diffractometry, and combinations thereof. Suitable X-ray diffractometry peaks may be, for example, at 26° and 31°, which correspond to the (0 0 2) plane, the (2 1 1) plane, the (1 1 2) plane, and the (2 0 2) plane for the hydroxyapatite mineral phase. Particularly suitable X-ray diffractometry peaks may be, for example, at 26° and 31°, which correspond to the (0 0 2) plane, the (1 1 2) plane, and the (3 0 0) plane for carbonate-substituted hydroxyapatite. Other suitable X-ray diffractometry peaks may be, for example, at 16°, 24°, and 33°, which correspond to the octacalcium phosphate mineral phase. Suitable spectra obtained by Fourier transform infrared spectrometry analysis may be, for example, a peak at 450-600 $cm^{-1}$, which corresponds to O—P—O bending, and a peak at 900-1200 $cm^{-1}$, which corresponds to asymmetric P—O stretch of the $PO_4^{3-}$ group of hydroxyapatite. Particularly suitable spectra peaks obtained by Fourier transform infrared spectrometry analysis may be, for example, peaks at 876 $cm^{-1}$, 1427 $cm^{-1}$, and 1483 $cm^{-1}$, which correspond to the carbonate ($CO_3^{2-}$) group. The peak for $HPO_4^{2-}$ may be influenced by adjusting the calcium and phosphate ion concentrations of the SBF used to prepare the mineral layer. For example, the $HPO_4^{2-}$ peak may be increased by increasing the calcium and phosphate concentrations of the SBF. Alternatively, the $HPO_4^{2-}$ peak may be decreased by decreasing the calcium and phosphate concentrations of the SBF. Another suitable peak obtained by Fourier transform infrared spectrometry analysis may be, for example, a peak obtained for the octacalcium phosphate mineral phase at 1075 $cm^{-1}$, which may be influenced by adjusting the calcium and phosphate ion concentrations in the simulated body fluid used to prepare the mineral layer. For example, the 1075 $cm^{-1}$ peak may be made more distinct by increasing the calcium and phosphate ion concentrations in the simulated body fluid used to prepare the mineral layer. Alternatively, the 1075 $cm^{-1}$ peak may be made less distinct by decreasing the calcium and phosphate ion concentrations in the simulated body fluid used to prepare the mineral layer.

Energy dispersive X-ray spectroscopy analysis may also be used to determine the calcium/phosphate ratio of the mineral layer. For example, the calcium/phosphate ratio may be increased by decreasing the calcium and phosphate ion concentrations in the SBF. Alternatively, the calcium/phosphate ratio may be decreased by increasing the calcium and phosphate ion concentrations in the SBF. Analysis of the mineral layers by energy dispersive X-ray spectroscopy allows for determining the level of carbonate ($CO_3^{2-}$) substitution for $PO_4^{3-}$ and incorporation of $HPO_4^{2-}$ into the mineral layers. Typically, the SBF includes calcium and phosphate ions in a ratio of from about 10:1 to about 0.2:1, including from about 2.5:1 to about 1:1.

Further, the morphology of the mineral layers may be analyzed by scanning electron microscopy, for example Scanning electron microscopy may be used to visualize the morphology of the resulting mineral layers. The morphology of the resulting mineral layers may be, for example, a spherulitic microstructure, plate-like microstructure, and/or a net-like microstructure. Suitable average diameters of the spherulites of a spherulitic microstructure may be, for example, from about 2 µm to about 42 µm. Particularly suitable average diameters of the spherulites of a spherulitic microstructure may be, for example, from about 2 µm to about 4 µm. In another embodiment, particularly suitable average diameters of the spherulites of a spherulitic microstructure may be, for example, from about 2.5 µm to about 4.5 µm. In another embodiment, particularly suitable average diameters of the spherulites of a spherulitic microstructure may be, for example, from about 16 µm to about 42 µm.

Suitable microparticle sizes can range from about 1 µM to about 100 µM in diameter. Microparticle diameter can be measured by methods known to those skilled in the art such as, for example, measurements taken from microscopic images (including light and electron microscopic images), filtration through a size-selection substrate, and the like.

Further, the nanostructure morphology of the mineral layer(s) can be analyzed by scanning electron microscopy, for example Scanning electron microscopy can be used to visualize the nanostructure morphology of the resulting mineral layer(s). The morphology of the resulting mineral layer(s) can be, for example, plate-like nanostructures. With a plate-like microstructure, the mineral layers include plates having an average diameter of from about 100 nm to about 1500 nm and an average pore size ranging from about 200 nm to about 750 nm. In one particularly suitable embodiment, when used in a plate-like nanostructure, the mineral layers include calcium, phosphate, hydroxide and bicarbonate.

Figure 1B:
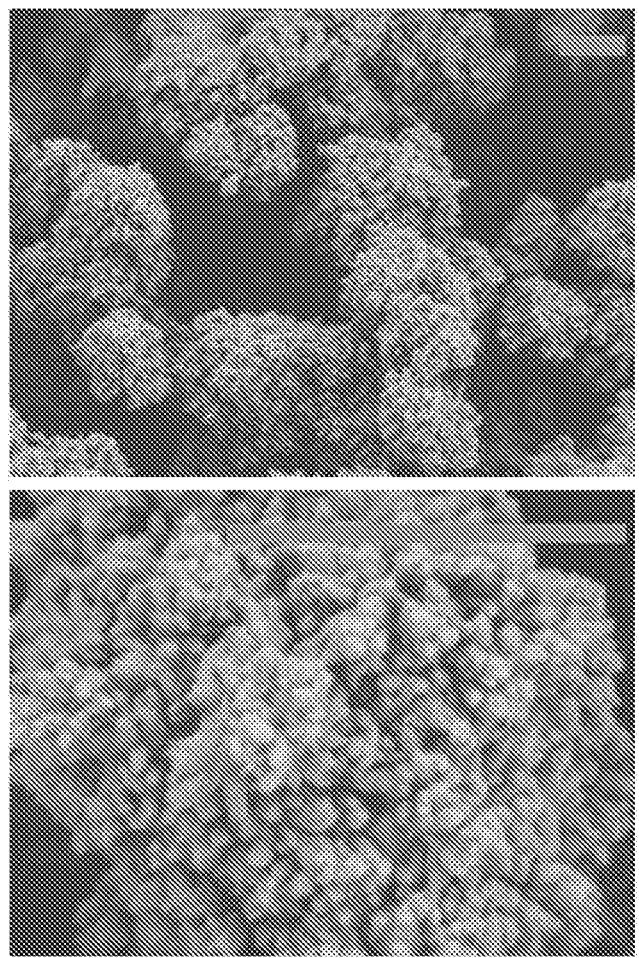
FIG. 1B is a scanning electron micrograph of mineral coated microparticles (MCMs) prepared using the methods described in Example 1.
Figure 1C:
FIG. 1C depicts a mineral layer with a needle-like morphology. Incubation of hydroxyapatite powder in mSBF containing 4.2 mM sodium bicarbonate and 1 mM sodium fluoride results in a mineral coating with a needle-like morphology. Scale bar=500 nm.

In yet other embodiments, the mineral layers have a needle-like microstructure, including needles that fill out the coating and do not show observable/measurable pores. Suitably, the needles range from about 10 nm to about 750 mm in length. An exemplary mineral layer having a needle-like microstructure is shown in FIG. 1C. In one particularly suitable embodiment, when used in a needle-like nanostructure, the mineral layers include calcium, phosphate, hydroxide, bicarbonate, and fluoride.

The method further includes contacting a polynucleotide with the mineral layer. Any polynucleotide as known in the art may be contacted with the mineral layer for use in the method of non-viral transfection. Suitable polynucleotides may be, for example, oligonucleotides, small interfering RNAs (siRNAs), messenger RNA (mRNA), short hairpin RNAs (shRNAs), and RNA aptamers. Particularly suitable ribonucleic acids include messenger RNAs (mRNA). Suitable RNAs also include RNAs with chemically modified bases such as incorporation of 5-methylcytidine, pseudouridine (Ψ), 2-thiouridine, $N_1$-methyl-pseudouridin, the combination of 5-methylcytidine and N1-methyl-pseudouridine, the combination of 5-methylcytidine and pseudouridine (Ψ) containing mRNAs.

In one embodiment, the polynucleotide is in the form of a polynucleotide complex. In particular, nucleic acids are mixed in solution with cationic lipids, polymers, or mineral ions to form polynucleotide liposomes, polysomes, or mineral complexes respectively. Example lipid reagents include Lipofectamine 2000, Lipofectamine 3000, ViaFect. Example cationic polymers include polyethylenimine (in its branched and unbranched forms). Example mineral ions include calcium and phosphate ions. Once formed, the polynucleotide complex is then adsorbed using the methods discussed herein.

The polynucleotides may encode any protein of interest (also referred to herein as bioactive peptide). For example, the polynucleotides may encode bioactive polypeptides including cytokines and growth factors. Particularly suitable bioactive polypeptides may be, for example, proteins involved in the growth and the repair of bone such as, for example, bone morphogenetic protein 1 (BMP1), bone morphogenetic protein 2 (BMP2), bone morphogenetic protein 3 (BMP3), bone morphogenetic protein 4 (BMP4), bone morphogenetic protein 5 (BMP5), bone morphogenetic protein 6 (BMP6), bone morphogenetic protein 7 (BMP7), bone morphogenetic protein 8a (BMP8a), epidermal growth factor (EGF), platelet-derived growth factor alpha polypeptide (PDGFA), platelet-derived growth factor beta polypeptide (PDGFB), platelet derived growth factor C (PDGFC), platelet derived growth factor D (PDGFD), platelet derived growth factor AB (PDGFAB), vascular endothelial growth factor A (VEGF-A), placenta growth factor (PlGF), vascular endothelial growth factor B (VEGF-B), vascular endothelial growth factor C (VEGF-C), vascular endothelial growth factor D (VEGF-D), transforming growth factor beta 1 (TGF-β1), transforming growth factor beta 2 (TGF-β2), transforming growth factor beta 3 (TGF-β3), anti-mullerian hormone (AMH), artemin (ARTN), growth-differentiation factor-1 (GDF1), growth-differentiation factor-2 (GDF2), growth-differentiation factor-3 (GDF3), growth-differentiation factor-3A (GDF3A), growth-differentiation factor-5 (GDF5), growth-differentiation factor-6 (GDF6), growth-differentiation factor-7 (GDF7), growth-differentiation factor-8 (GDF8), growth-differentiation factor-9 (GDF9), growth-differentiation factor-10 (GDF10), growth-differentiation factor-11 (GDF11), growth-differentiation factor-15 (GDF15), neurotrophic factor (GDFN), inhibin alpha chain (INHA), inhibin beta A chain (INHBA), inhibin beta B chain (INHBB), inhibin beta C chain (INHBC), inhibin beta E (INHBE), left-right determination factor 1 (LEFTY1), left-right determination factor 2 (LEFTY2), myostatin (MSTN), NODAL, neurturin (NRTN), persephin (PSPN), fibroblast growth factor 1 (FGF1), fibroblast growth factor 2 (FGF2), fibroblast growth factor 3 (FGF3), fibroblast growth factor 4 (FGF4), CBFA1/RUNX2, OSTERIX, SRY-box containing gene 9 (SOX9), Interleukin 1 Receptor Antagonist (IL1RA), Interleukin 10 (IL10), Chondroitinase ABC and Neurotrophin-3 (NT3), hepatocyte growth factor (HGF), granulocyte colony-stimulating factor (G-CSF), macrophage colony-stimulating factor (M-CSF), interleukin 6 (IL6), brain-derived neurotropic factor (BDNF), neurotrophin-4 (NT-4), nerve growth factor (NGF), insulin-like growth factor 1 (IGF-1), insulin-like growth factor-2 (IGF-2), fibroblast growth factor 21 (FGF21), human growth hormone (HGH) and combinations thereof.

Adsorption of the polynucleotide to the mineral coated microparticles can be tailored by changing the mineral constituents (e.g., high carbonate and low carbonate microspheres), by changing the amount of mineral coated microparticles incubated with the polynucleotide, by changing the concentration of polynucleotide in the incubation solution, and combinations thereof.

The polynucleotide adsorbed to the mineral layer of the mineral coated microparticle is released as the mineral layer degrades. Mineral degradation can be controlled such that the mineral layer can degrade rapidly or slowly. Mineral layer dissolution rates can be controlled by altering the mineral layer composition. For example, mineral layers that possess higher carbonate substitution degrade more rapidly. Mineral layers that possess lower carbonate substitution degrade more slowly. Alterations in mineral layer composition can be achieved by altering ion concentrations in the modified simulated body fluid during layer formation. Modified simulated body fluid with higher concentrations of carbonate, 100 mM carbonate for example, results in layers which degrade more rapidly than layers formed in modified simulated body fluid with physiological carbonate concentrations (4.2 mM carbonate).

To incorporate the polynucleotide within the mineral coated microparticle, polynucleotide is included in the simulated body fluid during the mineral coating process. To adsorb polynucleotide on different layers of the mineral coated microparticle, mineral coated microparticles are incubated in a solution containing the polynucleotide after the formation of each layer. Some layers may have no polynucleotide adsorbed onto the surface. To adsorb polynucleotide complexes on the surface mineral layer, polynucleotide complexes are first formed via incubation of the polynucleotide with the complexation reagent, and then incubated with the mineral coated microparticle.

The method further includes contacting the mineral coating microparticle including the polynucleotide with an injured tissue. It has been advantageously found that the MCMs can efficiently and effectively deliver the polynucleotides to the injured tissue, thereby encoding therapeutically relevant released bioactive polypeptides that promote regenerative healing or remodeling of fibrous scar tissue.

As used herein, the methods include contacting the MCMs with injured tissue in a subject in need thereof. As used herein, a subject "in need thereof" refers to an individual having a tissue injury, and in particular, having a chronic wound. As used herein, "chronic wound" refers to conditions such as spinal cord injuries from lacerations or contusions, diabetic ulcer, and the like, which have historically been treated using recombinant proteins. As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of subjects "in need thereof" of assistance in addressing one or more specific conditions noted herein), not all subjects will fall within the subset or subclass of subjects as described herein. In particular, the subject in need thereof is a human. The subject in need thereof can also be, for example, a research animal such as, for example, a non-human primate, a mouse, a rat, a rabbit, a cow, a pig, and other types of research animals known to those skilled in the art.

Methods of Sustaining Delivery of Bioactive Polypeptides with the MCMs

In another aspect, it has further been found that the MCMs described herein can additionally serve to sequester and stably release overexpressed bioactive polypeptides (e.g., cytokines, growth factor) to a subject in need thereof, allowing for the sustained delivery of the bioactive polypeptides. In general, the methods include contacting the mineral coated microparticle including the polynucleotide adsorbed thereto as described above with at least one cell (e.g., a cell at the site of the injured tissue). Over time, the microparticle mineral coating degrades, locally secreting a bioactive polypeptide encoded by the polynucleotide to cells.

To contact the microparticle with the cell, any method known in the art can be used. For example, in one embodiment, the microparticles are directly injected into the injured site to contact the cell. In another embodiment, the microparticles can be included in a formulation and the formulation can be administered to the injured site to contact the cell.

Formulations including the microparticles can then be prepared by adding a carrier to the mineral coated microparticles having the polynucleotide adsorbed to the mineral coating. Suitable carriers include water, saline, isotonic saline, phosphate buffered saline, Ringer's lactate, and the like. In one embodiment, the carrier is a pharmaceutically acceptable carrier. As understood by those skilled in the art, pharmaceutically acceptable carriers, and, optionally, other therapeutic and/or prophylactic ingredients must be "acceptable" in the sense of being compatible with the other ingredients of the formulation and not be harmful to the recipient thereof. Suitable pharmaceutically acceptable carrier solutions include water, saline, isotonic saline, phosphate buffered saline, Ringer's lactate, and the like. The compositions of the present disclosure can be administered to animals, preferably to mammals, and in particular to humans as therapeutics per se, as mixtures with one another or in the form of pharmaceutical preparations, and which as active constituent contains an effective dose of the active agent, in addition to customary pharmaceutically innocuous excipients and additives.

In one embodiment, a carrier including an active agent can be added to mineral coated microparticles having the active agent adsorbed to the mineral coating to prepare a formulation including bound active agent (active agent adsorbed to the mineral coated microparticle) and unbound active agent. In another embodiment, a carrier not including an active agent can be added to mineral coated microparticles having the active agent adsorbed to the mineral to prepare a formulation including bound active agent.

In particularly suitable formulation embodiments, the formulations include both bound and unbound polynucleotide. Without being bound by theory, it is believed that injection of a formulation including mineral coated microparticles with bound polynucleotide and unbound polynucleotide allows unbound polynucleotide to provide an immediate effect whereas bound polynucleotide is sequestered by its adsorption to the mineral coated microparticle and provides a sustained effect as the mineral coating degrades and releases the polynucleotide.

As used herein, an effective amount, a therapeutically effective amount, a prophylactically effective amount and a diagnostically effective amount is the amount of the unbound polynucleotide and the polynucleotide adsorbed to the mineral coated microparticle needed to encode bioactive polypeptide in an amount sufficient to elicit the desired biological response following administration.

Formulations for parenteral administration (e.g. by injection, for example bolus injection or continuous infusion) can be presented in unit dose form in ampoules, pre-filled syringes, small volume infusion or in multi-dose containers with and without an added preservative. The formulations can take such forms as suspensions, solutions, or emulsions in oily or aqueous vehicles, and may contain formulation agents such as suspending, stabilizing and/or dispersing agents. Alternatively, the mineral coated microparticles with polynucleotide may be in powder form, obtained for example, by lyophilization from solution, for constitution with a suitable vehicle, e.g. sterile, pyrogen-free water, before use.

In one aspect, the present disclosure is directed to a mineral coated microparticle comprising at least one polynucleotide incorporated within a mineral layer and at least one polynucleotide adsorbed to the mineral layer.

As disclosed herein, to incorporate the polynucleotide within the mineral coated microparticle, polynucleotide is included in the simulated body fluid during the mineral coating process. Particularly suitable polynucleotides include those described herein.

As described herein, the polynucleotide can be adsorbed to the mineral layer. The polynucleotide can also be incorporated within the mineral layer of the mineral coated microparticle, as described herein. The polynucleotide can further be adsorbed to the mineral layer and incorporated within the mineral layer of the mineral coated microparticle, as described herein. Different polynucleotides can be adsorbed to or incorporated within the mineral layer.

As noted above, upon contact between the microparticle and the cell, bioactive polypeptide encoded by the polynucleotide is released. The released bioactive polypeptide can then further be sequestered by the mineral coated microparticle. More particularly, the mineral coatings are comprised of positive and negative charges as well as acidic and basic moieties. The mineral binds bioactive polypeptides via electrostatic interactions between the coating and the polypeptide. The highly nanoporous nature of the coating creates a large surface area that affords a high peptide binding capacity.

After binding of bioactive polypeptides, the mineral coating releases the polypeptides over time. The method of release involves gradual surface-mediated degradation by leaching of calcium, phosphate, and bicarbonate from the mineral coating. Bicarbonate undergoes subsequent hydrolysis, further promoting dissolution of the mineral coating and release of bioactive peptide. Incorporation of greater bicarbonate increases the coating dissolution rate and bioactive polypeptide release.

Sustained delivery of the bioactive polypeptides can be determined to obtain bioactive polypeptide release values that mimic established therapeutic levels of the bioactive polypeptides. The mass of mineral coated microparticles (with the polynucleotide adsorbed) required to produce a desired concentration of the encoded and released bioactive polypeptide over a period of time can be calculated beforehand. For example, a single bolus injection of the polynucleotide that provides the desired therapeutic effect can be delivered in a sustained manner over the desired period of time by obtaining the bioactive polypeptide release values from the mineral coated microparticles. Then, the mass of mineral coated microparticles needed to deliver the polynucleotide for encoding sufficient bioactive polypeptide to provide the therapeutic effect of a desired period of time can be calculated. The localized and sustained delivery platform offers the benefit of continuous therapeutic levels of the bioactive polypeptide at the injury site without the requirement for multiple injections.

Effective dosages are expected to vary substantially depending upon the polynucleotide(s) used and the specific disease, disorder, or condition treated. Because of the rapid and sustained delivery of the bioactive polypeptides released and sequestered by the microparticles, suitable dosages of microparticles/formulations are expected to be less than effective dosages of bioactive polypeptides delivered via bolus injections. As described herein, mineral coated microparticles can be prepared to deliver an effective amount of the bioactive polypeptide over the course of several days. Thus, administration of formulations provide a sustained release of the bioactive polypeptide during degradation of the mineral layer of the mineral coated microparticle to maintain the effect over the course of hours to days as desired.

Formulations of the present disclosure can be administered to subjects in need thereof. As used herein, "a subject" (also interchangeably referred to as "an individual" and "a patient") refers to animals including humans and non-human animals. Accordingly, the compositions/formulations, devices and methods disclosed herein can be used for human and veterinarian applications, particularly human and veterinarian medical applications. Suitable subjects include warm-blooded mammalian hosts, including humans, companion animals (e.g., dogs, cats), cows, horses, mice, rats, rabbits, primates, and pigs, preferably a human patient.

EXAMPLES

Example 1

In this Example, polynucleotide adsorption to mineral coated microparticles was analyzed. The mineral coated microparticles with polynucleotide adsorbed thereto were then analyzed for transfection efficiency.

Mineral coated microparticles (MCM) were fabricated by incubating hydroxyapaptite microparticles in mSBF (2× calcium and phosphate concentration of human serum), refreshed daily, for 7 days, as described in Suárez-Gonzalez et al. (Acta Biomater. 8 (2012)). Carbonate concentration in the mSBF were varied (4.2 mM or 100 mM) with 1 mM sodium fluoride to form MCMs with different coating compositions. A schematic of this process is shown in FIG. 1A. Further, the resulting MCMs are shown in FIG. 1B.

Nucleic acids were condensed with Lipofectamine 2000 for pDNA and Lipofectamine messenger max for mRNA to form a polynucleotide lipid complex and then the complex was adsorbed to the mineral layer of the MCMs. Particularly, MCMs were incubated in 30 µg/mL of complex in OPTI-MEM, ThermoFisher.

Once adsorbed, these complex-laden MCMs were then used to deliver the nucleic acids through either direct addition to 2D cell monolayers, incorporation into the interior of 3D cell aggregates, or via direct injection in vivo (schematic in FIG. 2A). For 2D cell culture, soluble polynucleotide complexes or complex-laden MCMs were directly added to the cell culture media.

Figure 2B:
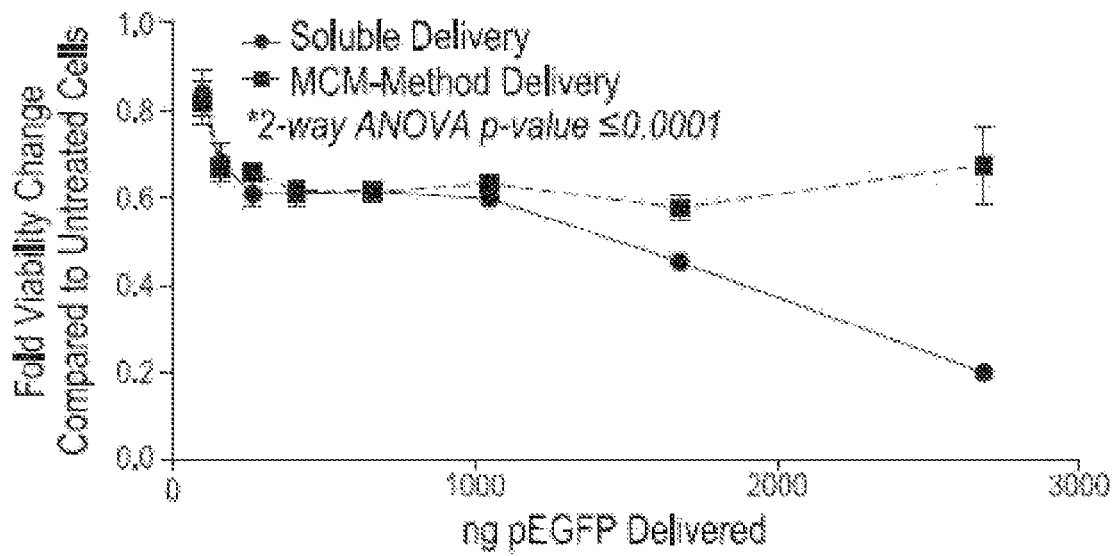
FIG. 2B depicts the Resazurin reduction assay (CellTiter-Blue) measuring metabolic activity of transfected human dermal fibroblasts (hDF) as analyzed in Example 1.
Figure 2C:
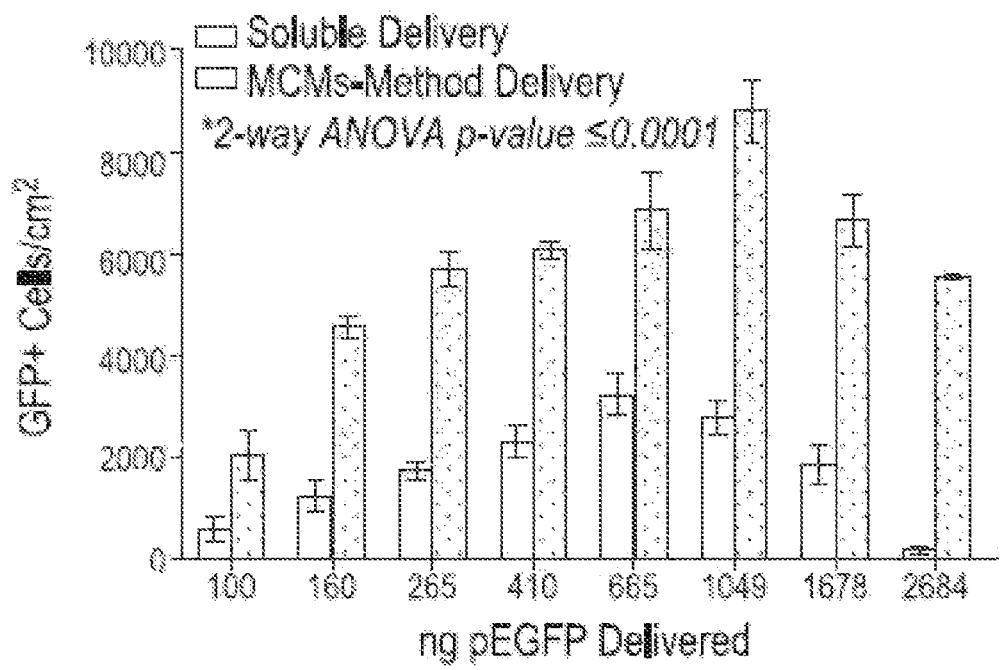
FIG. 2C depicts transfection efficiency of hDF using standard and MCM-mediated transfection of pEGFP with Lipofectamine2000.

Transfection efficiency was measured via epifluorescence after delivery of a green fluorescent protein-encoding gene (EGFP). Transgene expression was measured via luminescence after delivery of a firefly luciferase-encoding gene (FLuc). The results are shown in FIGS. 2B & 2C.

Example 2

In this Example, the ability of the MCMs to sequester overexpressed bioactive polypeptide encoded by polynucleotide delivered by the MCMs was analyzed.

Figure 3A:
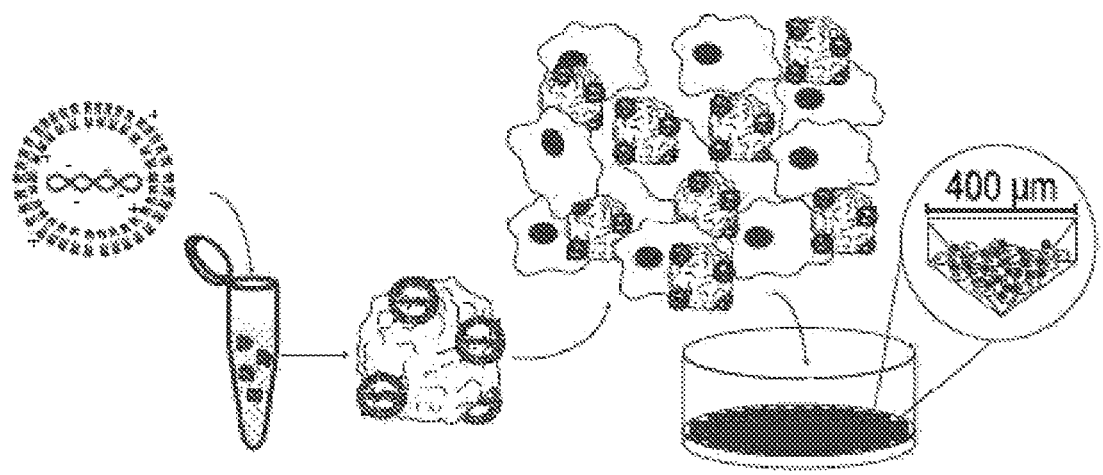
FIG. 3A is a schematic of MCM incorporation into a cell aggregate during forced aggregation.
Figure 3B:
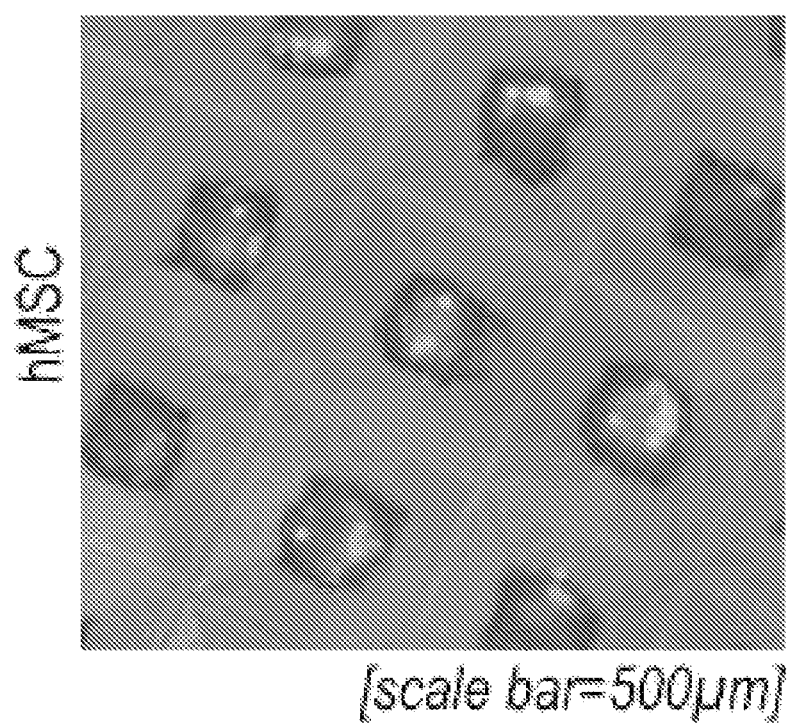
FIG. 3B depicts that MCM-mediated delivery of pEGFP enabled efficient transfection of hMSC aggregates.
Figure 3C:
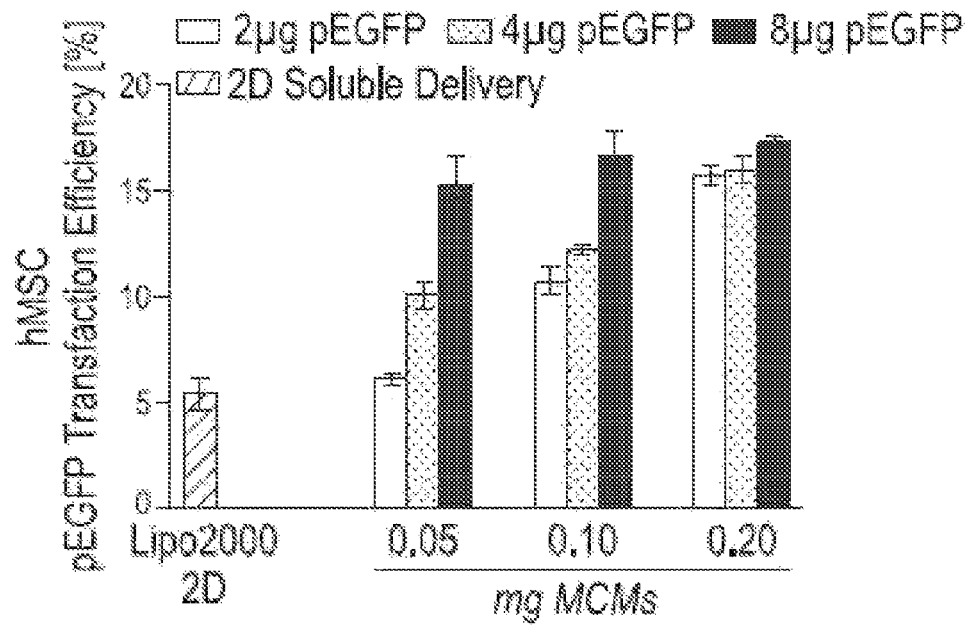
FIG. 3C depicts quantification of MCM-mediated transfection efficiency in hMSC aggregates.
Figure 3D:
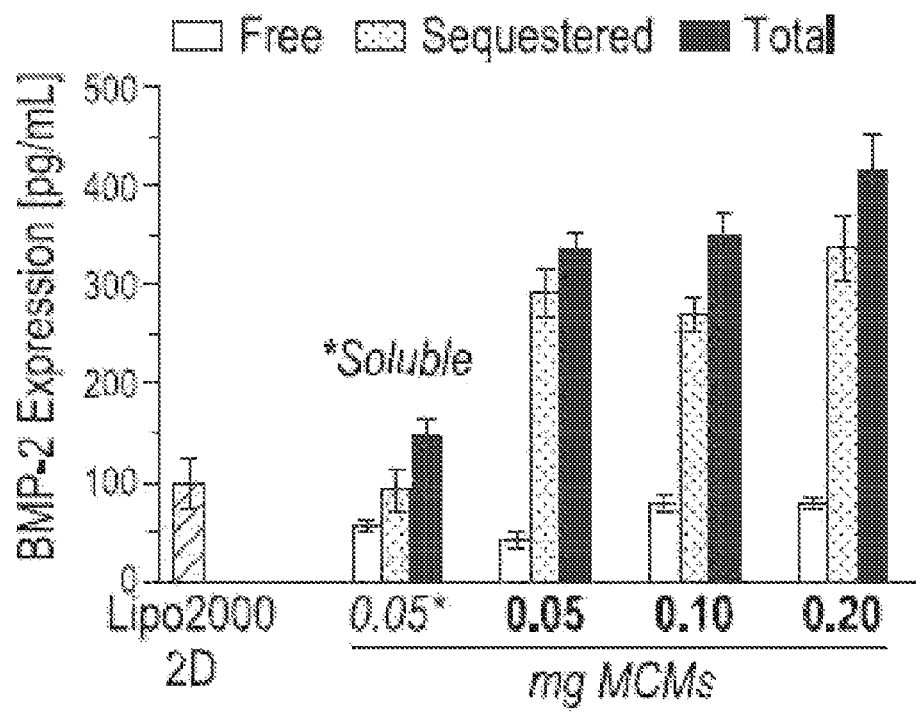
FIG. 3D depicts resulting bone morphogenic protein-2 (BMP-2) production via MCM-mediated transfection of pBMP-2 in hMSC aggregates. "Free" and "Sequestered" represent BMP-2 separately quantified from the cell culture media and from dissolved mineral coatings, respectively.

As shown in FIG. 3A, MCMs were incubated and rotated at room temperature for 30 minutes with pBMP-2 or pEGFP complexed with Lipofectamine 2000 in OPTI-MEM, ThermoFisher. The complex-laded MCMs were mixed with singularized human mesenchymal stem cells (hMSCs) and then centrifuged in 400 µm (diagonal length) pyramidal agarose microwells to create hMSC aggregates containing pBMP-2 or pEGFP complex laden MCMs. As shown in FIG. 3B, green fluorescence of hMSC aggregates containing pEGFP complex-laden MCMs was measured via epifluorescence microscopy of intact aggregates. Transfection efficiency of MCM-transfected hMSC aggregates was determined using flow cytometry. Transfection was carried out in aggregates with 0.05, 0.1, and 0.2 mg of MCMs; 2, 4, and 8 µg of pEGFP; and 15000 cells per cell aggregate (FIG. 3C) Similar transfections as in FIG. 3C were carried out using pBMP-2 complexes (FIG. 3D). Aggregates were trypsinized and spun down. The supernatant was collected to create "free" fraction, and the spun down fraction was treated with 100 mM EDTA to create a "sequestered" fraction. BMP-2 protein concentration of these two fractions was measured using sandwich ELISA.

Example 3

In this Example, the ability of the MCMs to sequester bFGF and increase bFGF-mRNA induced proliferation was analyzed.

Figure 4A:
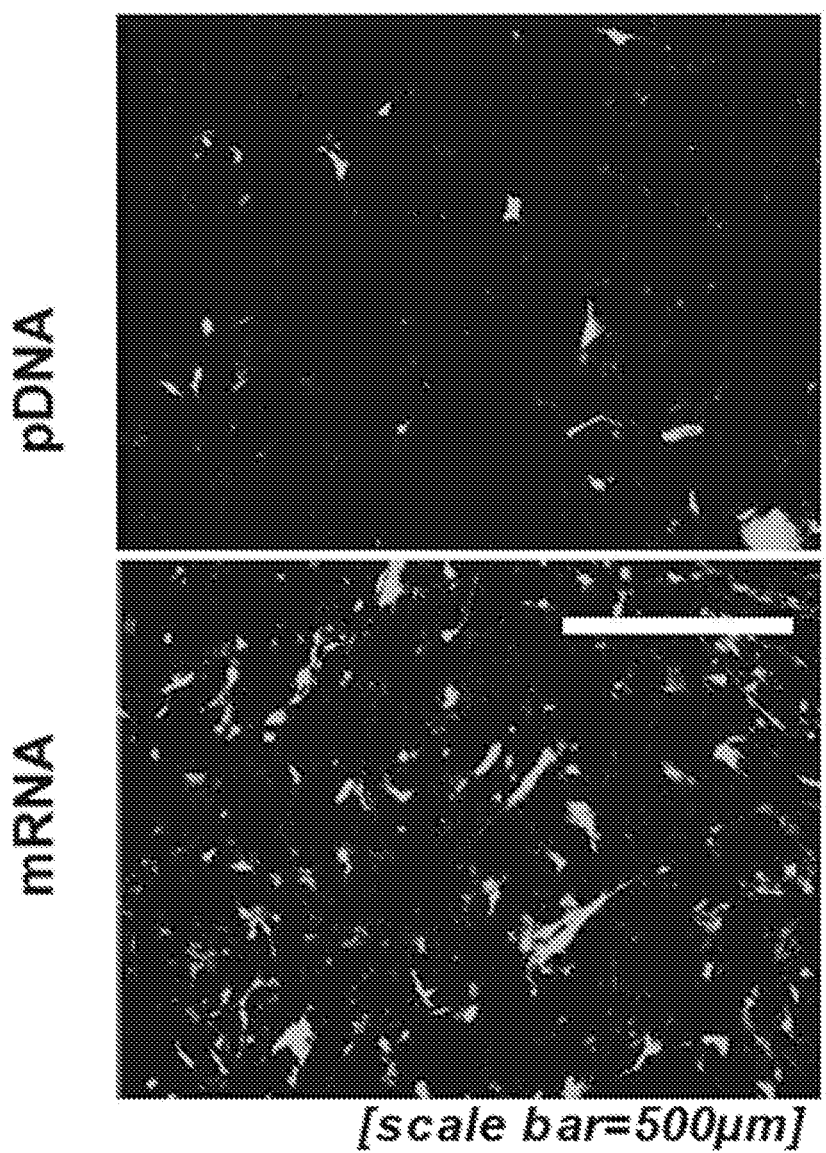
FIG. 4A are representative images of transfection efficiency from EGFP-pDNA and -mRNA delivery in mitomycin C-treated hDF.
Figure 4B:
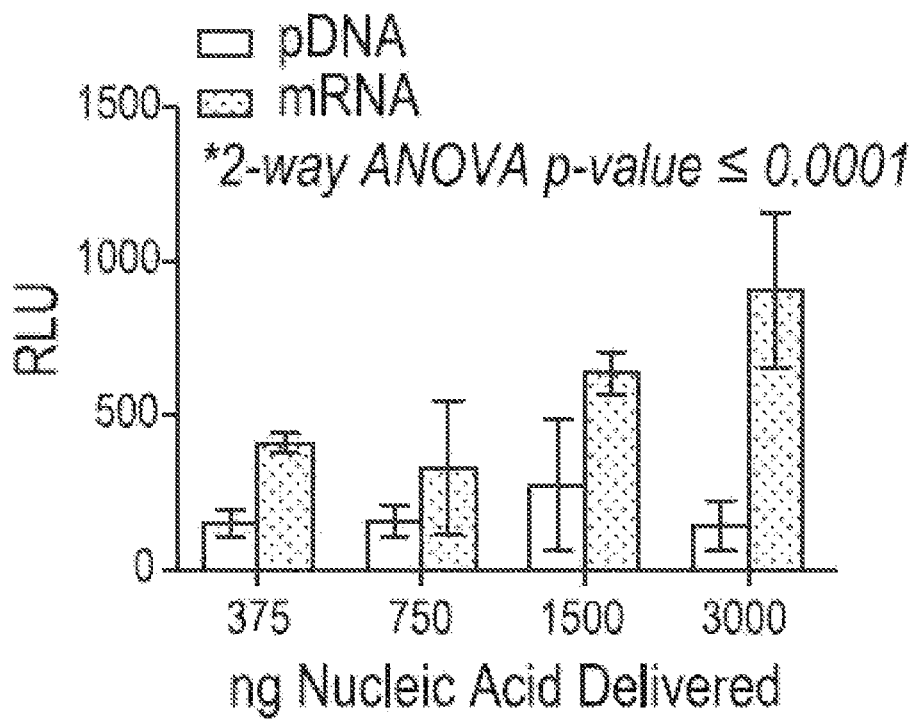
FIG. 4B and FIG. 4C are comparisons of transgene expression (FIG. 4B) from FLuc-pDNA and -mRNA, and duration (FIG. 4C) from FLuc-mRNA with and without MCMs (MCM+/−) in mitomycin C-treated hDF.
Figure 4C:
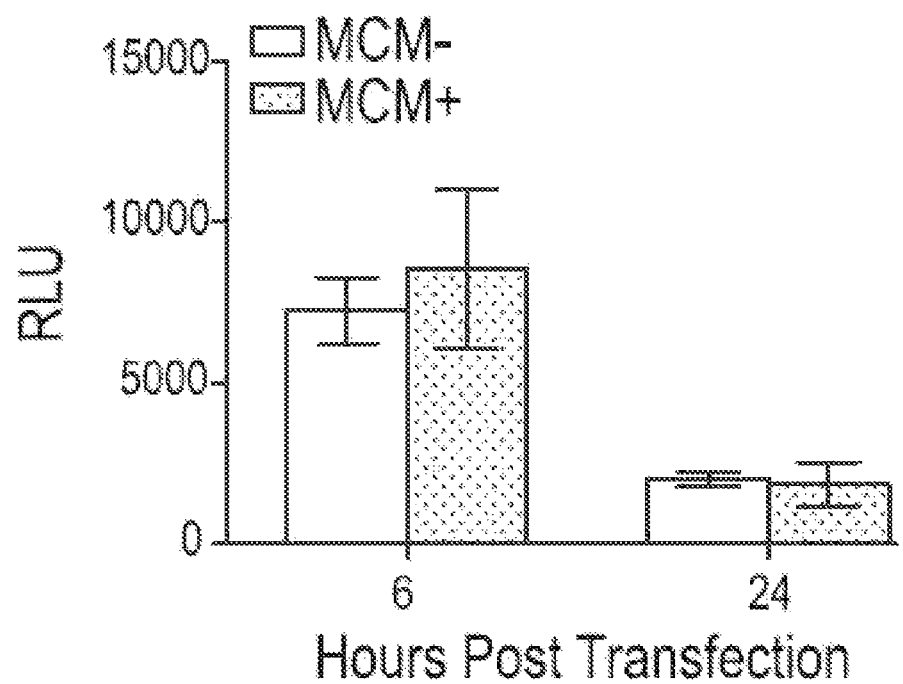
Figure 4D:
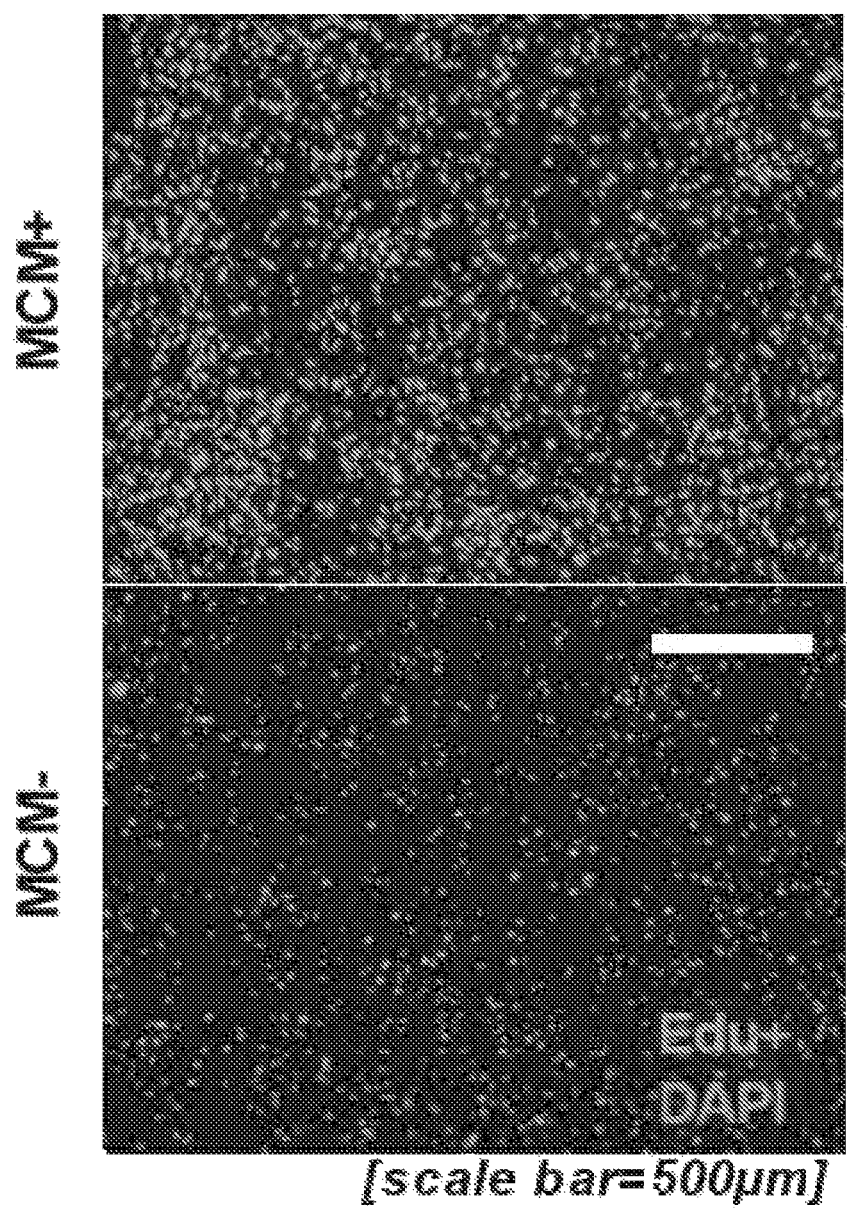
FIG. 4D depicts bFGF-mediated proliferation in serum-starved hDF with nuclei in blue (DAPI) and S-phase+ cells in red (EdU+).
Figure 4E:
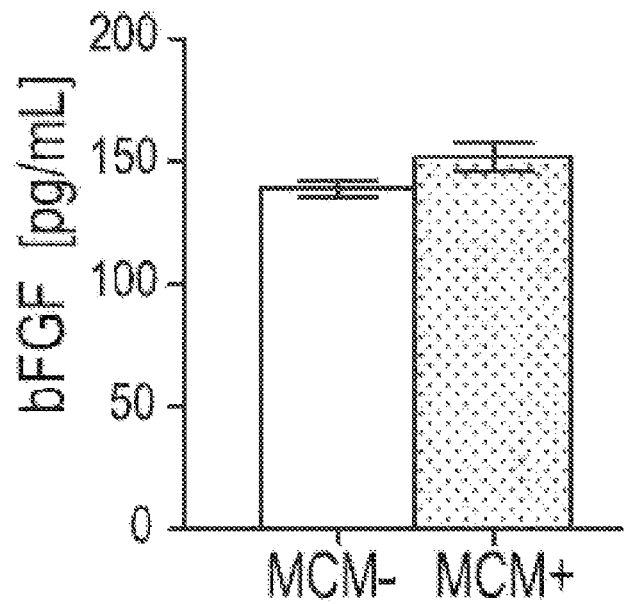
FIG. 4E, FIG. 4F, and FIG. 4G depict total bFGF production (FIG. 4E) measured via enzyme-linked immunosorbent assay (ELISA) after bFGF-mRNA delivery with and without MCMs (MCM+/−), quantification of MCM influence on hDF proliferation (FIG. 4F) in response to bFGF-mRNA delivery 5 days after transfection, and quantification of free bFGF in the cell culture media and sequestered bFGF in the mineral layers for the MCM-mRNA delivery strategy (FIG. 4G).
Figure 4F:
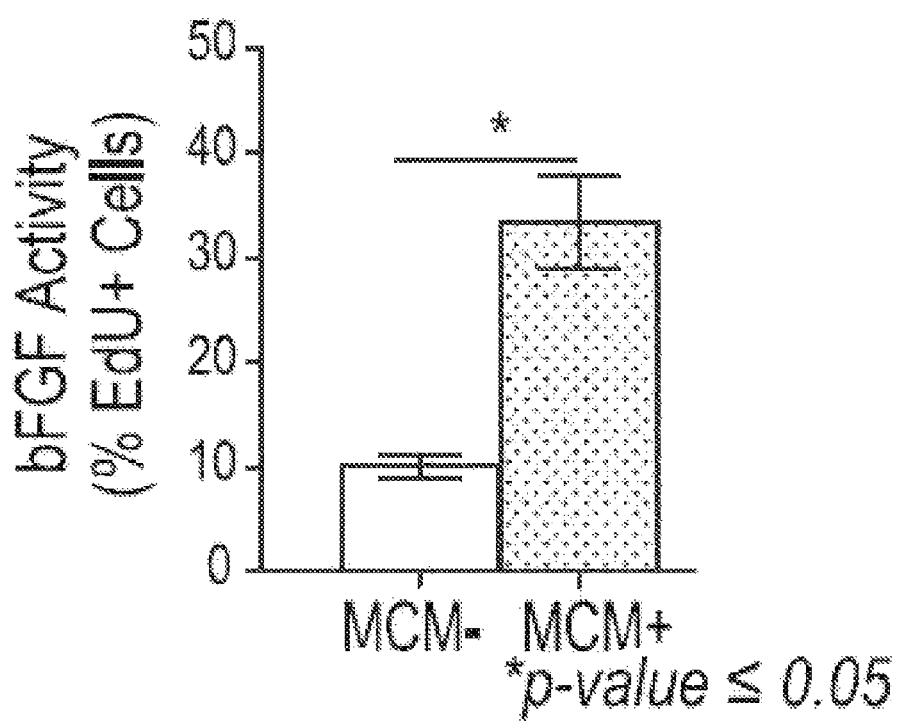
Figure 4G:
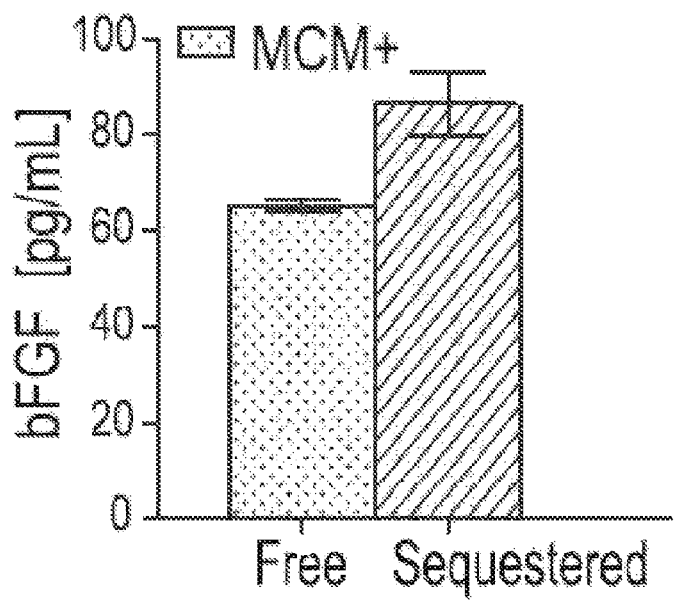

Human dermal fibroblasts (hDF) were treated with mitomycin-C (10 µg/mL) for three hours post transfection with pEGFP or mRNA-EGFP using Lipofectamine 2000 and Lipofectamine messenger max, respectively (FIG. 4A). Green fluorescence was monitored via epifluorescence microscopy. In FIG. 4B and FIG. 4C, hDFs were treated as in FIG. 4A and transfected with firefly luciferase (pFLuc) and mRNA-FLuc complexed with Lipofectamine messenger max (both in solution without MCMs and adsorbed on to the MCMs). Luminescence was measured using the Luciferase Assay System (Promega) at 6 and 24 hours (FIG. 4C). In FIG. 4E, FIG. 4F, and FIG. 4G, hDFs were serum-starved (DMEM+0.5% fetal bovine serum) for 24 hours prior to transfection of basic fibroblast growth factor (bFGF)-encoding mRNA (both in solution without MCMs and adsorbed on the MCMs). hDFs were assayed for proliferation using the Click-Edu kit (ThermoFisher) at 2 and 5 days and assessed for Edu incorporation using epifluorescence microscopy. In FIG. 4E, FIG. 4F, and FIG. 4G, bFGF production was measured via sandwich ELISA. "Free" bFGF refers to the bFGF in the culture media. "[S]equestered bFGF" refers to the bFGF released after washing of the culture well and chelation with EDTA.

Example 4

Figure 5A:
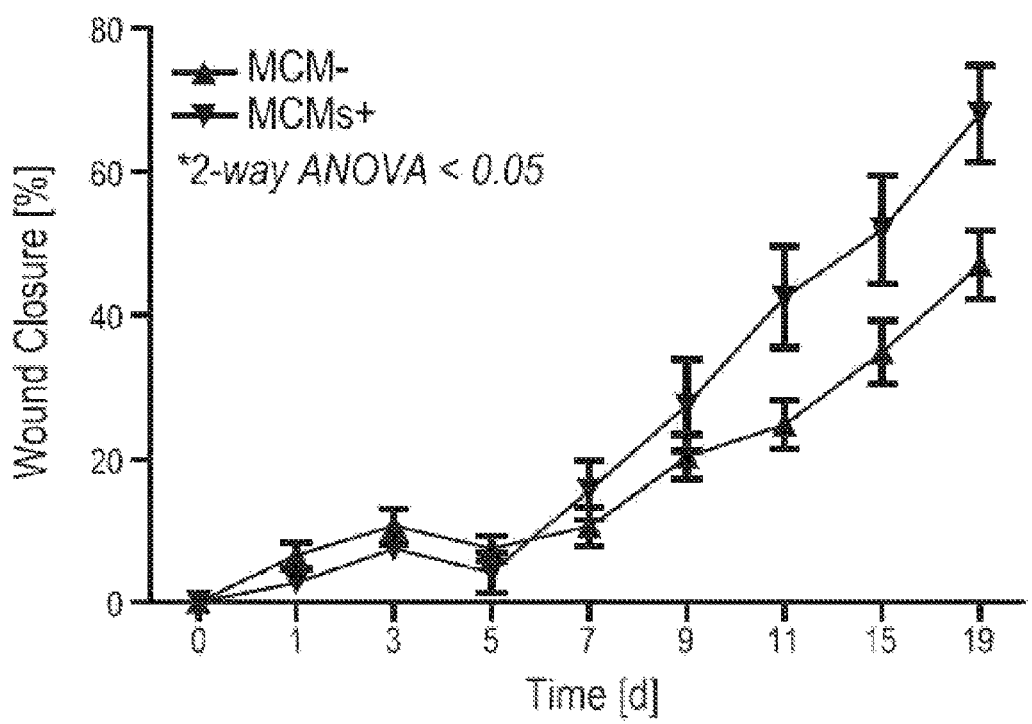
FIG. 5A depicts dermal wound healing in a diabetic murine model in response to bFGF-mRNA delivered with and without MCMs (MCM+/−) measured by wound diameter as a percentage of initial wound.
Figure 5B:
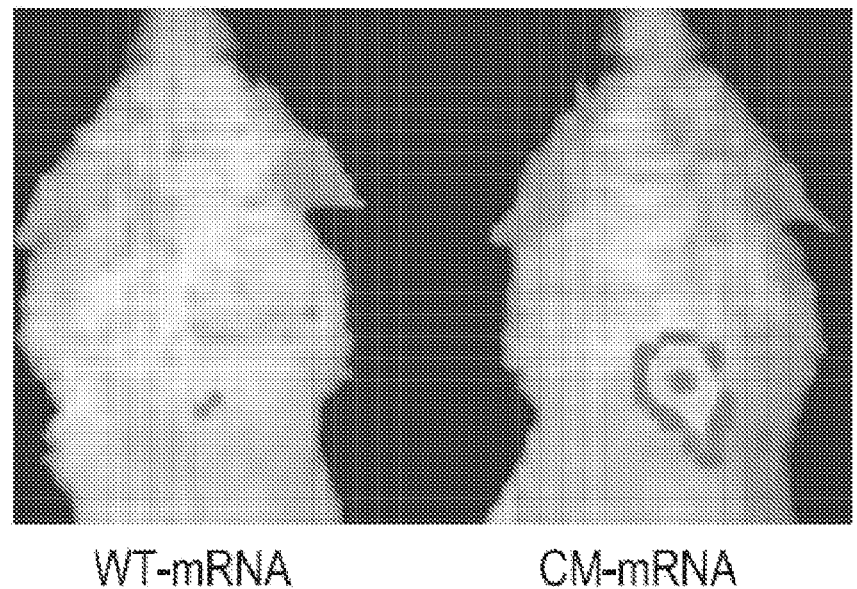
FIG. 5B depicts in vivo imaging (IVIS) of luminescence from delivery of wild type—(WT) and chemically modified—(CM) FLuc-mRNA with MCMs.
Figure 5C:
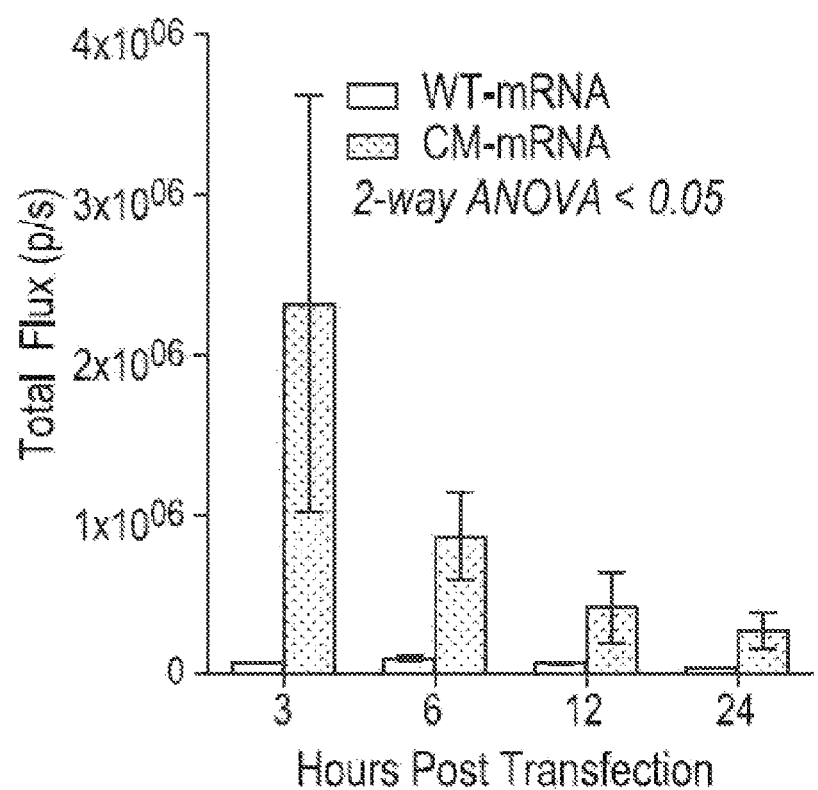
FIG. 5C depicts quantification and time course of luminescence flux measured via IVIS after WT- and CM-FLuc delivery with MCMs.

In this Example, the effects of MCMs and mRNA chemical modifications on in vivo gene delivery were determined.

db/db mutant C57BLKS mice (Jackson Labs) were used in a diabetic dermal wound healing assay. Two ~1 cm dermal wounds were created via manual excision of the dermal tissue on the mouse back. Treatments (bFGF mRNA complexed with Lipofectamine messenger max in solution without MCMs or adsorbed onto MCMs) were applied topically within 1 hour of wound generation. The wounds were covered with Transpore (3M) tape to prevent infection and animal tampering with the wound. Wound diameter was measured on the indicated days post-surgery (FIG. 5A). Percent wound closure was measured as percent diameter of original wound diameter. Wild type and mRNA containing the chemically modified ribonucleobases 5-methyl cytosine and psuedouridine (TriLink Bio) were complexed with Lipofectamine messenger max and then injected subcutaneously into BALB/cJ mice (Jackon Labs). Luminescence was monitored and quantified after injection of 100 mg D-luciferin/mg body weight. Results are shown in FIG. 5A, FIG. 5B, and FIG. 5C.

Example 5

In this Example, a model secreted fluorescent protein visualizes a "overexpressed and sequester" mechanism was utilized.

Figure 6A:
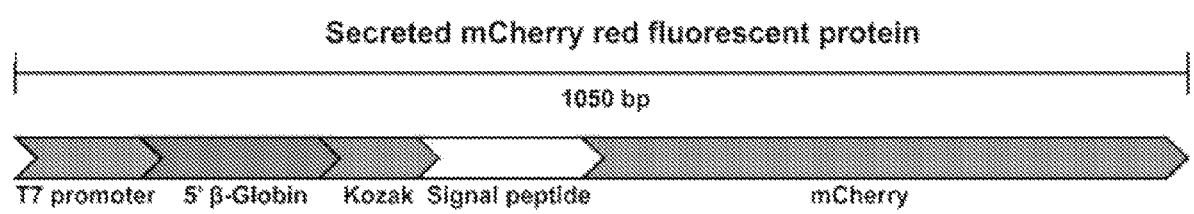
FIG. 6A depicts a schematic for 1050 bp DNA template for model secreted protein. Template includes a T7 promoter, the 5' untranslated region (UTR) from human (β-globin, Kozak sequence, a signal peptide sequence from mouse matrix-metalloprotease 9 for cell secretion, and the mCherry coding sequence.
Figure 6B:
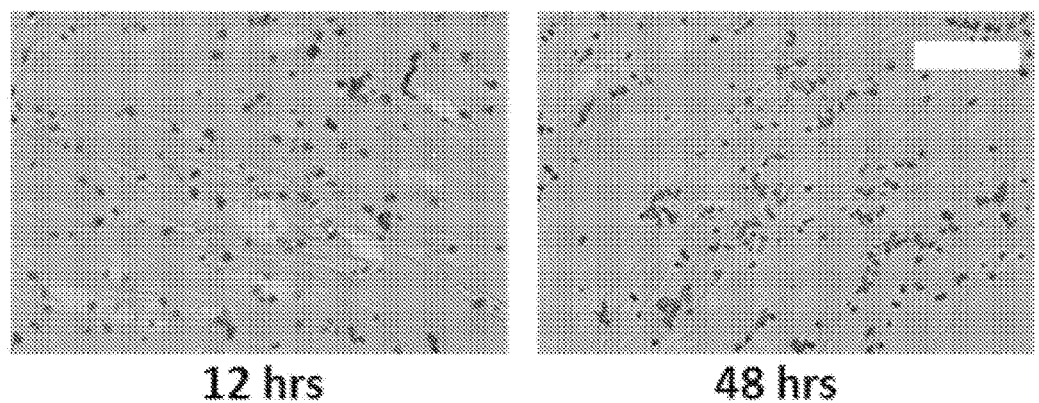
FIG. 6B depict merged phase and red fluorescence micrographs of MCMs cultured with hDF. (left) 12 hours post-transfection of the secreted mCherry-encoding mRNA with MCMs. Red fluorescence is observed in the cytoplasm and MCMs are not fluorescent at 12 hours. (right) 48 hrs post-transfection of the secreted mCherry-encoding mRNA with MCMs, cytoplasmic red fluorescence has subsided and MCMs are now fluorescent.
Figure 6C:
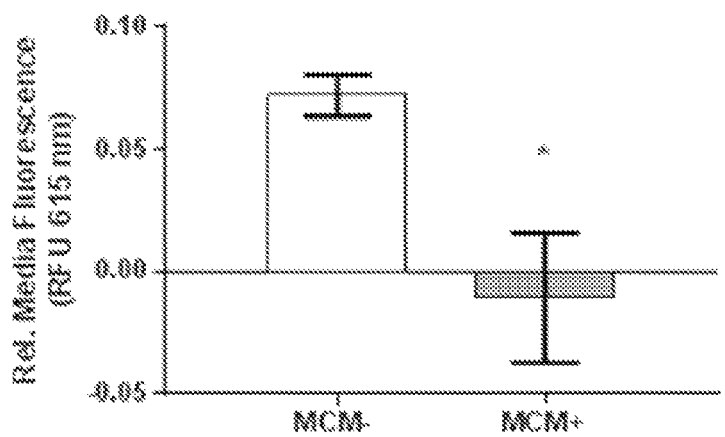
FIG. 6C depicts a graph of sequestration of secreted CM-mCherry reduces fluorescence of cell culture media. Red fluorescence of cell culture media measured via multi-plate reader of hDFs transfected with secreted mCherry mRNA with and without MCMs.
Figure 6D:
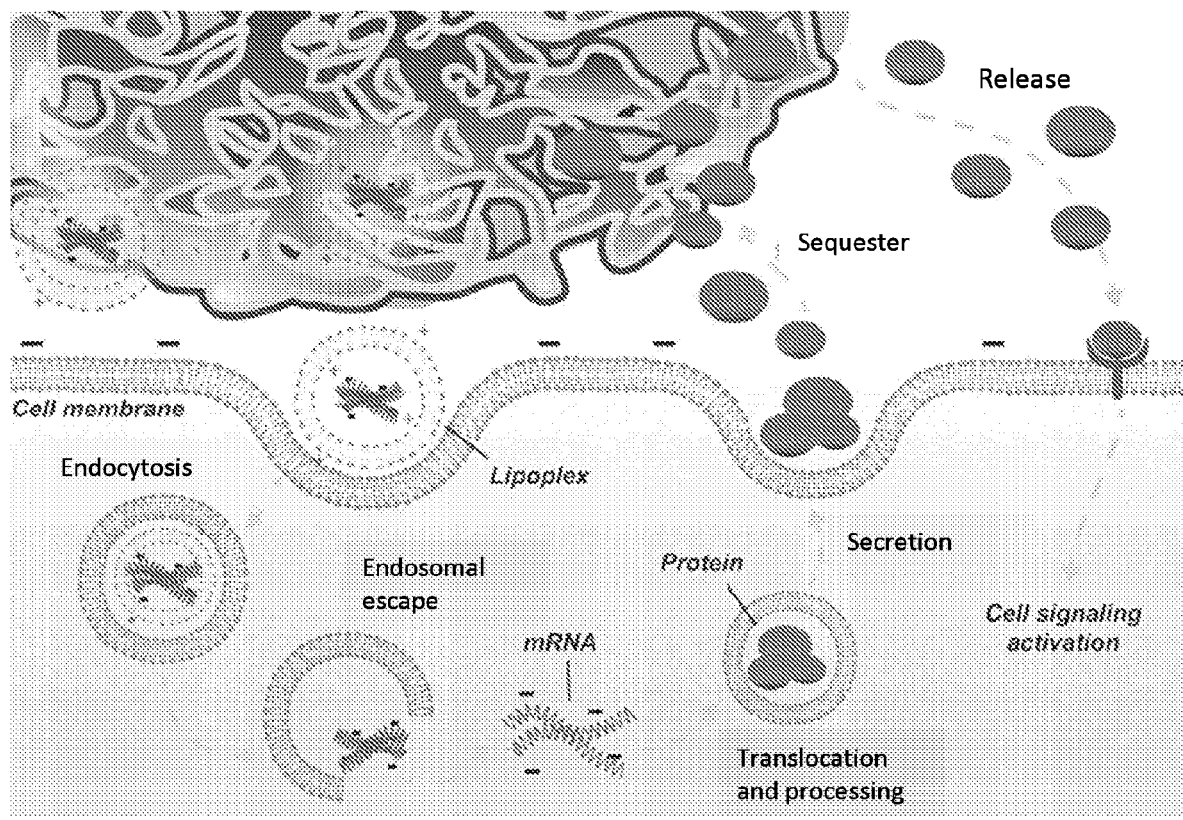
FIG. 6D depicts a schematic of "overexpress and sequester" mechanism. MCMs initially deliver mRNA complexed with a transfection reagent such as a cationic lipid (lipoplex). After endocytosis, and cytoplasmic delivery, the the mRNA can proceed directly to translation. After translation and processing, the MCMs used for initial delivery of the mRNA complexes bind and sequester the secreted protein. The protein is released from the mineral coating over time back to the cell, prolonging the biological response through increased duration of cell-signaling activation.
Figure 7A:
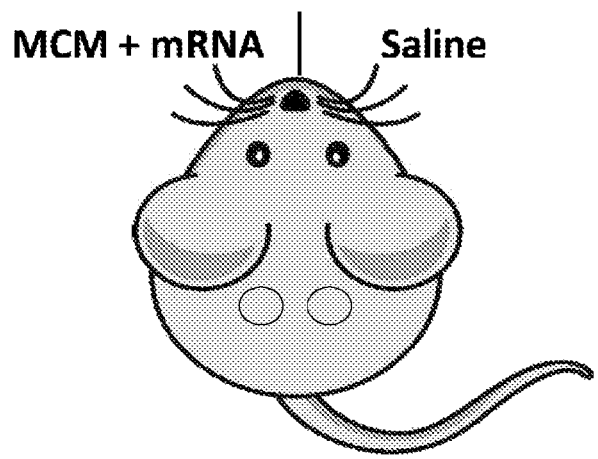
FIG. 7A depicts a schematic of animal treatments. db+/db+ mice with two dermal wounds received treatment in the left wound while the right wound served as a contralateral saline control to show extent of overexpressed protein localization.
Figure 7B:
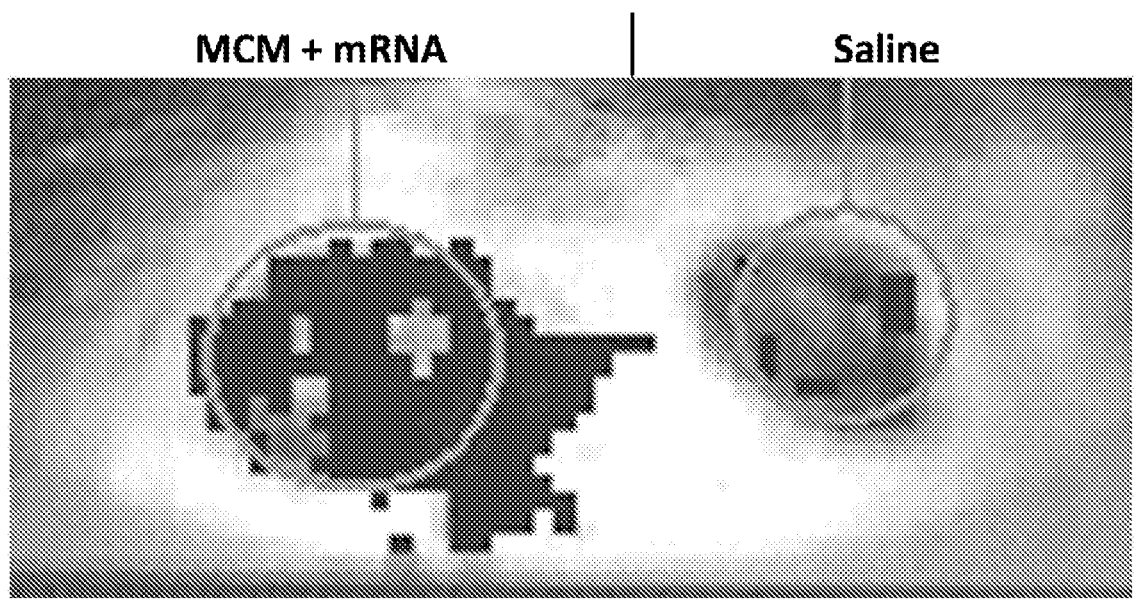
FIG. 7B depicts representative IVIS fluorescence image of CM-mCherry+MCM-treated dermal wound (left wound) and saline control (right wound) 48 hrs post-delivery.
Figure 7C:
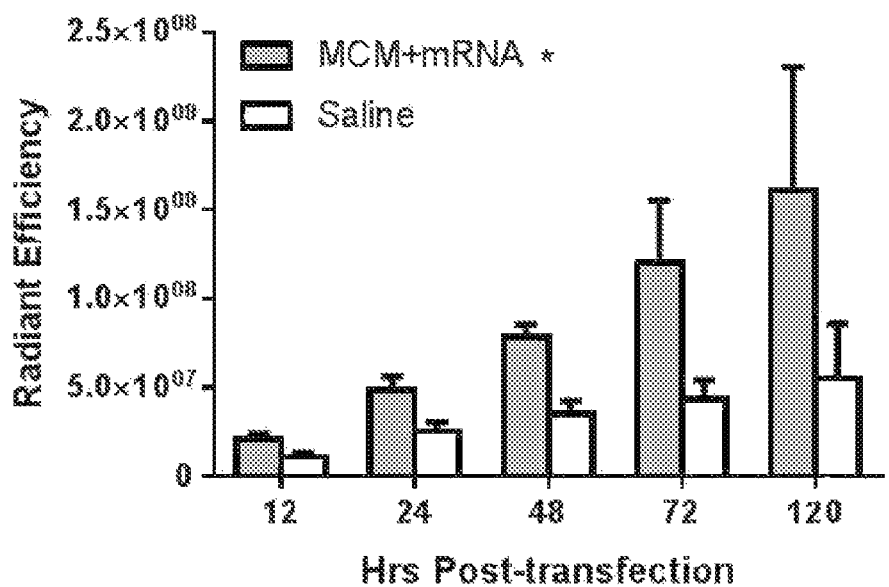
FIG. 7C and FIG. 7D depict graphs illustrating radiant efficiency of a region of interest defined by each wound perimeter for red fluorescence over 5 days in animals transfected with MCMs (FIG. 7C) and without (FIG. 7D). N=3*p-value <0.05 by two-way ANOVA.
Figure 7D:
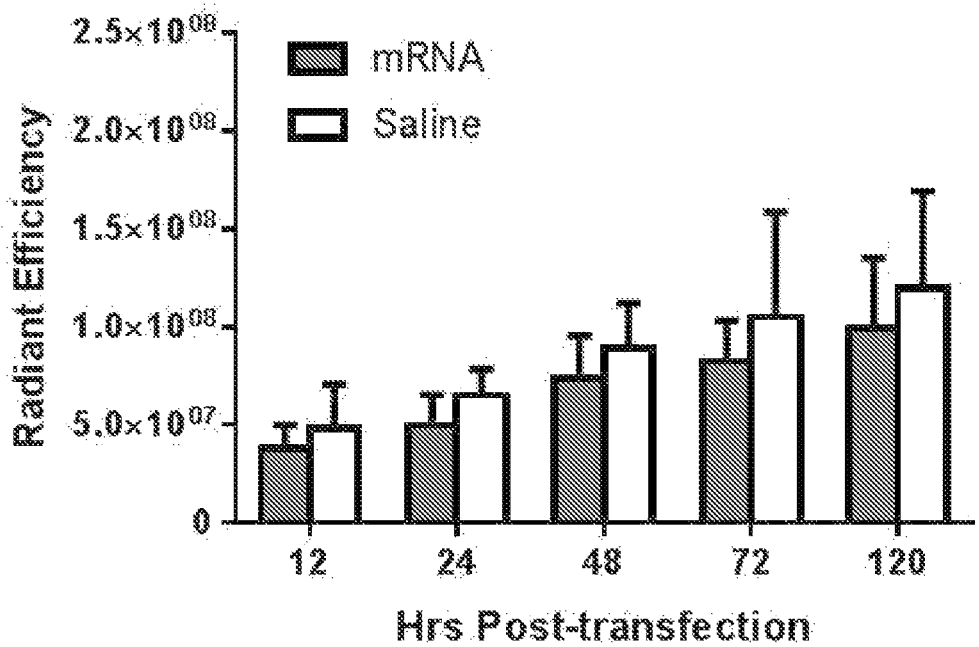

A mRNA transcript encoding for a secreted variant of mCherry fluorescent protein was used to observe the sequestering effect of MCMs (FIG. 6A). Red fluorescence was observed to co-localize with MCMs 48 hours post-transfection (FIG. 6B) and reduce the increase in media fluorescence observed in transfection without MCMs (FIG. 6C). This concept is schematically shown in FIG. 6D.

Example 6

In this Example, the effects of MCM-medicated mRNA delivery localized overexpressed protein to a dermal wound in vivo were determined.

db+/db+ mutant mice received two dermal wounds and were transfected with secreted mCherry mRNA with or without MCMs and contralateral saline control. The wounds were monitored for red fluorescence over time via IVIS and quantified for comparison. Results are shown in FIG. 7A, FIG. 7B, FIG. 7C, and FIG. 7D.

Example 7

Figure 8A:
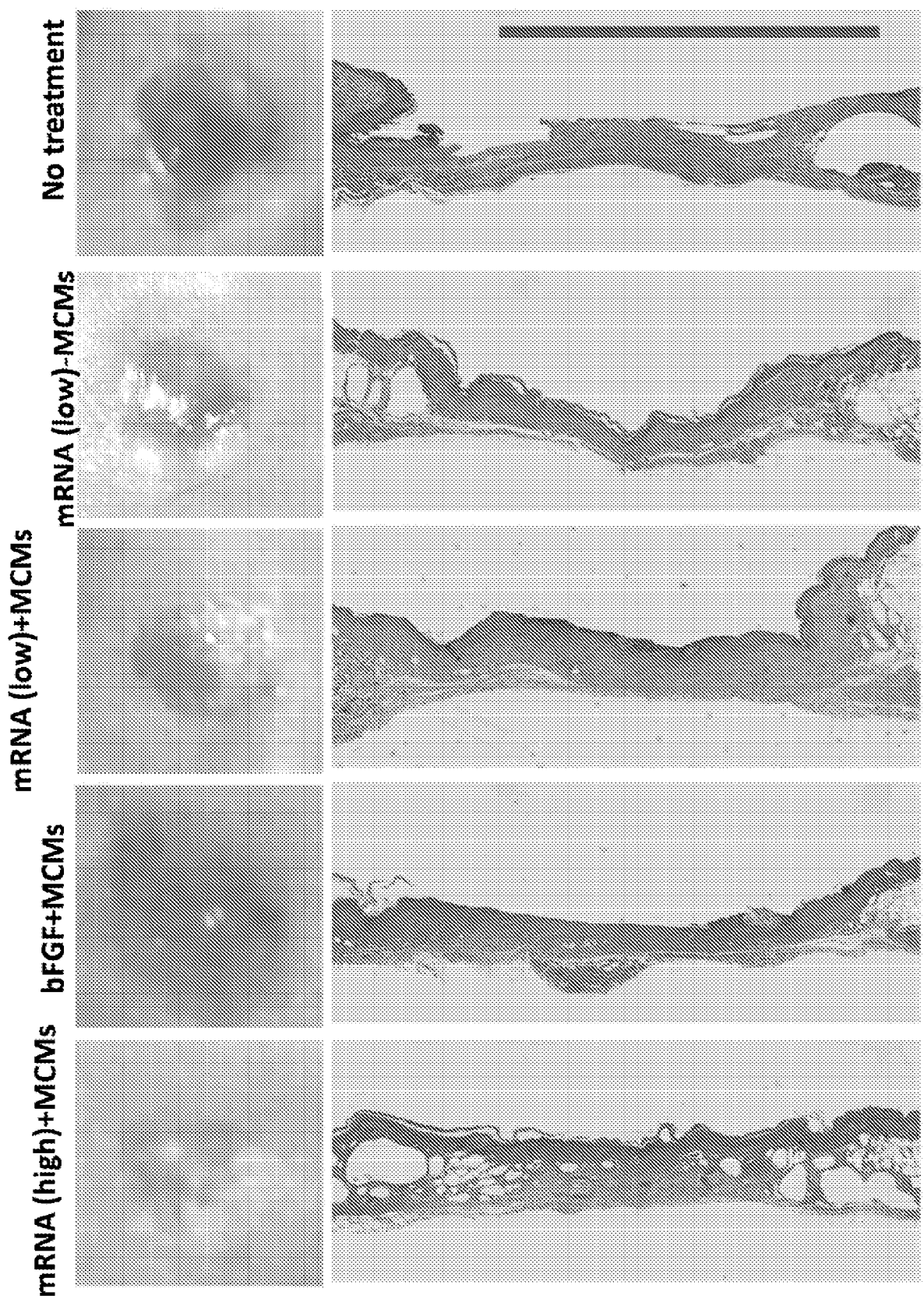
FIG. 8A depicts gross analysis of wounds and (right) representative histological images show improved wound closure and resolution for mbFGF treatment with MCMs relative to the no treatment control and other treatment groups.
Figure 8B:
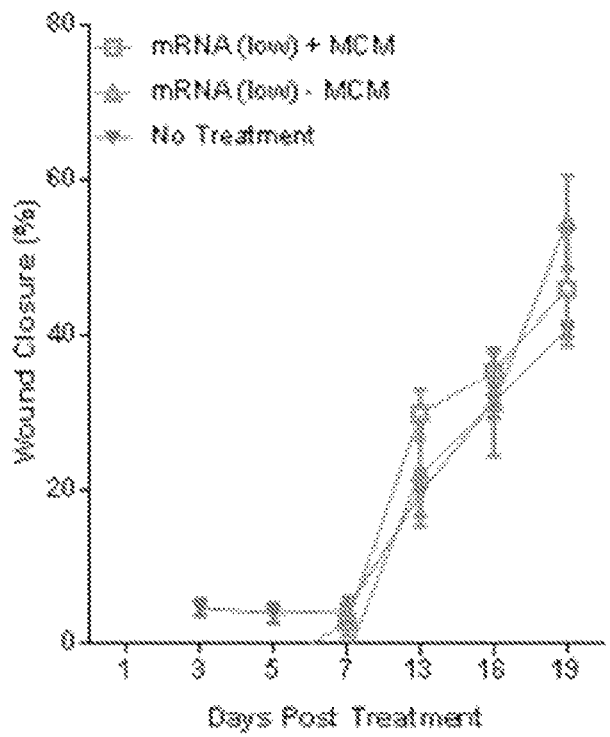
FIG. 8B and FIG. 8C depict wound closure rates plotted as % wound perimeter reduction vs time of (FIG. 8B) low dose mbFGF with and without MCMs, as well as (FIG. 8C) high dose mbFGF and recombinant bFGF all compared to a no treatment control. N=8-10*p-value <0.05 by two-way ANOVA with Dunnet's post hoc analysis relative to the no treatment control.
Figure 8C:
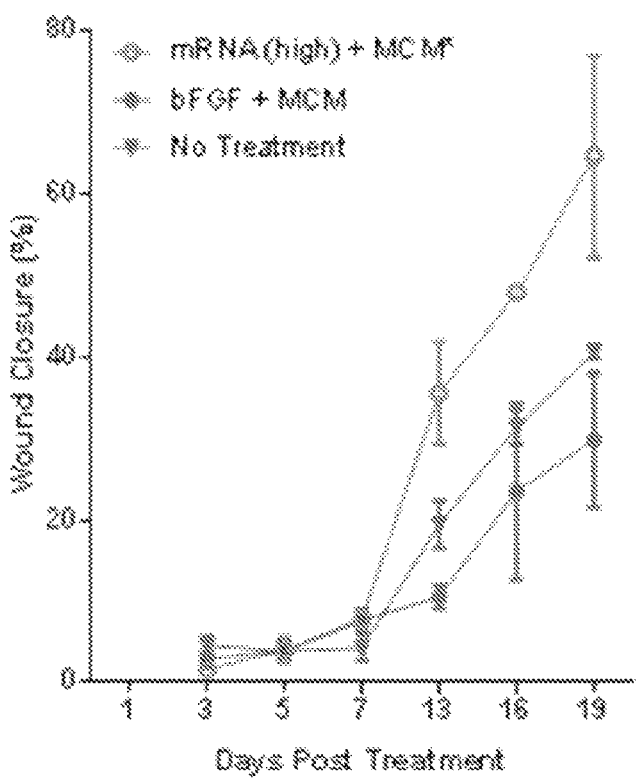
Figure 8D:
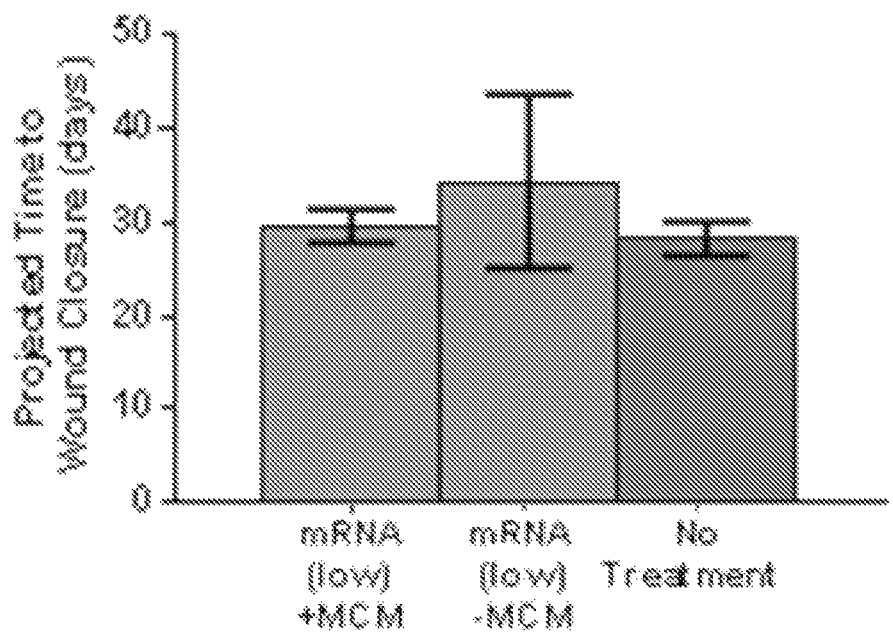
FIG. 8D and FIG. 8E depicts predicted time to complete wound closure based on exponential fit of perimeter over time for (FIG. 8D) low dose mbFGF with and without MCMs, and (FIG. 8E) high dose mbFGF and recombinant bFGF all compared to a no treatment control. N=8-10, †p-value <0.05 one-way ANOVA with Dunnet's post hoc analysis relative to each plotted measurement of the no treatment control.
Figure 8E:
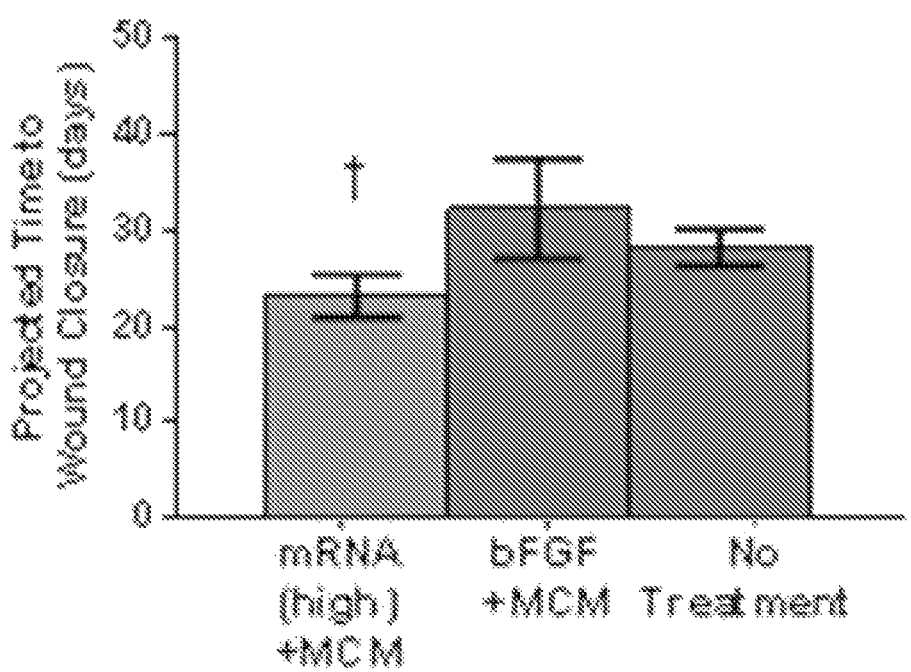
Figure 8F:
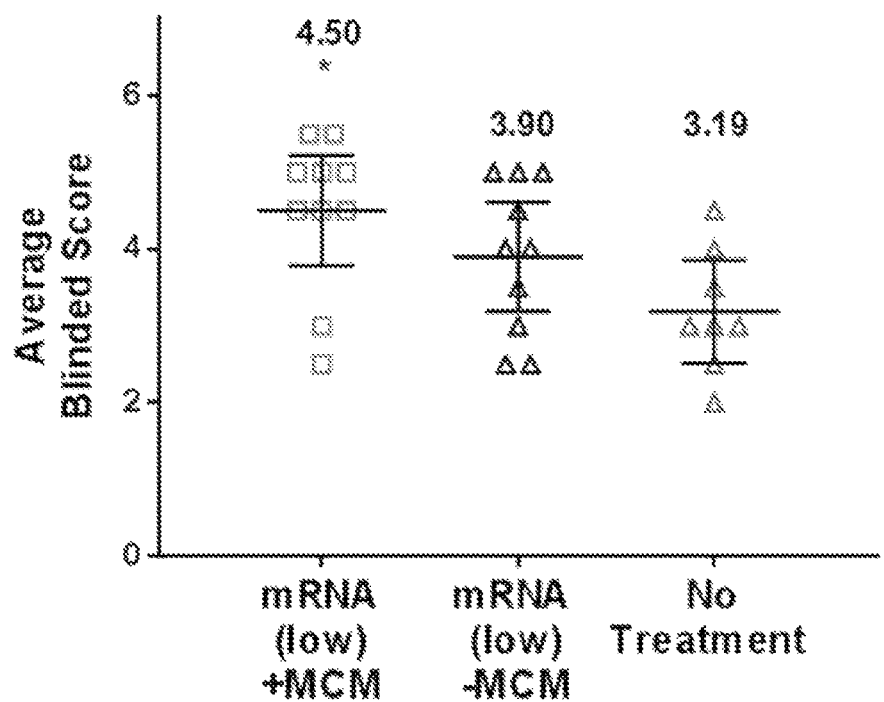
FIG. 8F and FIG. 8G depicts average wound histology score for each treatment group 19 days post treatment for (FIG. 8F) low dose mbFGF with and without MCMs, and (FIG. 8G) high dose mbFGF and recombinant bFGF all compared to a no treatment control. *p-value <0.05, ***p-value <0.001 by one-way ANOVA with Dunnet's post hoc analysis relative to the no treatment control.
Figure 8G:
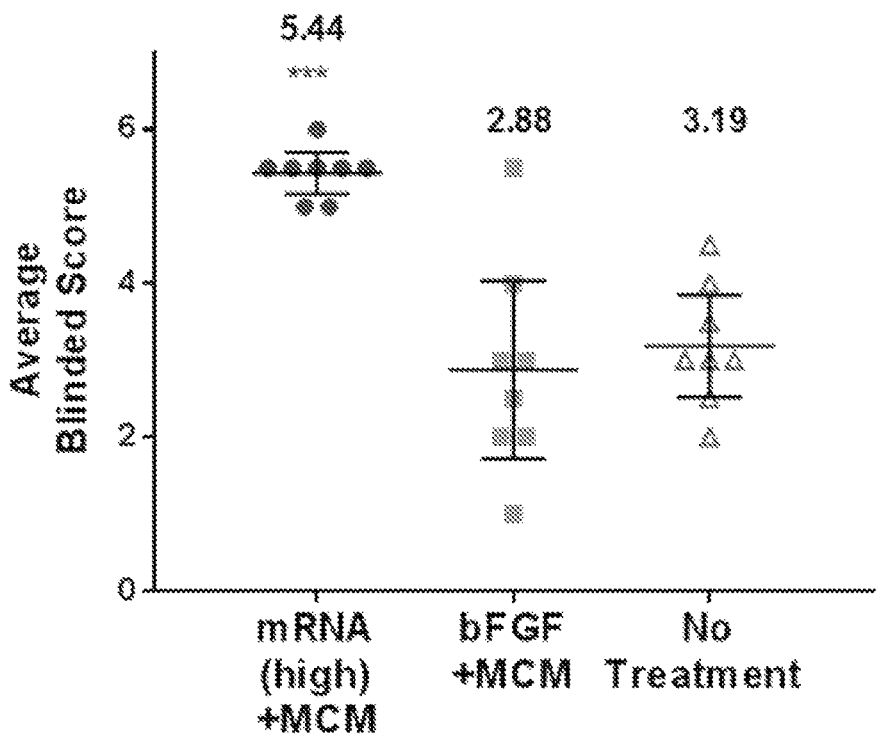

In this Example, the effects of MCM-mediated mbFGF delivery on wound closure rate and final wound resolution were determined.

db+/db+ mutant mice received two dermal wounds and the treatments described in FIG. 8A. The wounds were allowed to heal for 19 days, with wound perimeters measured at the timepoints listed in FIG. 8B. After 19 days, the animals were sacrificed and the tissue collected for histology. The excised wounds were sectioned transversely and stained with H&E. The stained tissues were scored by two people, blinded to the treatment groups, for the quality of wound resolution (FIG. 8F and FIG. 8G). Results are shown in FIG. 8A, FIG. 8B, FIG. 8C, FIG. 8D, FIG. 8E, FIG. 8F, and FIG. 8G.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of repairing injured tissue in a subject in need thereof, the method comprising:
    contacting a microparticle comprising a mineral layer with a polynucleotide selected from the group consisting of small interfering RNAs (siRNAs), messenger RNA (mRNA), short hairpin RNAs (shRNAs), and RNA aptamers, wherein the polynucleotide is adsorbed to the mineral layer; and
    contacting the microparticle with the injured tissue, wherein the polynucleotide is released, is taken up by cells of the injured tissue, and results in increased production of a bioactive peptide, wherein the bioactive polypeptide is selected from the group consisting of cytokines, growth factors, and combinations thereof;
    wherein the bioactive polypeptide secreted from the cells becomes sequestered with the microparticle, and subsequently is released as the mineral layer of the mineral coated microparticle degrades,
    wherein the injured tissue is a diabetic ulcer, and
    wherein the mineral layer is in the shape of a needle having an average length of from about 10 nm to about 750 nm.

2. The method of claim 1, wherein the microparticle comprises a core selected from the group consisting of polymers, ceramics, metals, glass, and combinations thereof.

3. The method of claim 2, wherein the core comprises one or more of beta-tricalcium phosphate (beta-TCP, β-TCP) and hydroxyapatite (HAP).

4. The method of claim 1, wherein the polynucleotide is in the form of a polynucleotide complex selected from the group consisting of a polynucleotide lipid liposome, polysome, mineral complex, and combinations thereof.

5. A method for sustained delivery of bioactive polypeptides, the method comprising:
    contacting a mineral coated microparticle comprising a mineral layer with a polynucleotide adsorbed thereto with at least one cell, wherein the mineral layer comprises calcium, phosphate, carbonate and combinations thereof, and wherein the polynucleotide encodes a bioactive polypeptide selected from the group consisting of cytokines, growth factors, and combinations thereof, wherein the polynucleotide is released, is taken up by the at least one cell of the injured tissue, and results in increased production of the bioactive peptide in the at least one cell;
    wherein the bioactive polypeptide secreted from the cells becomes sequestered with the microparticle via electrostatic interactions between the polypeptide and the microparticle, and subsequently is released as the mineral layer of the mineral coated microparticle degrades,
    wherein the injured tissue is a diabetic ulcer, and
    wherein the mineral layer is in the shape of a needle having an average length of from about 10 nm to about 750 nm.

6. The method of claim 5, wherein the bioactive polypeptide is selected from the group consisting of basic fibroblast growth factor (bFGF), epidermal growth factor (EGF), platelet-derived growth factor alpha polypeptide (PDGFA), platelet-derived growth factor beta polypeptide (PDGFB), platelet derived growth factor C (PDGFC), platelet derived growth factor D (PDGFD), platelet derived growth factor AB (PDGFAB), vascular endothelial growth factor A (VEGF-A), placenta growth factor (PlGF), vascular endothelial growth factor B (VEGF-B), vascular endothelial growth factor C (VEGF-C), vascular endothelial growth factor D (VEGF-D), transforming growth factor beta 1 (TGF-β1), transforming growth factor beta 2 (TGF-β2), transforming growth factor beta 3 (TGF-β3), anti-mullerian hormone (AMH), artemin (ARTN), growth-differentiation factor-1 (GDF1), growth-differentiation factor-2 (GDF2), growth-differentiation factor-3 (GDF3), growth-differentiation factor-3A (GDF3A), growth-differentiation factor-5 (GDF5), growth-differentiation factor-6 (GDF6), growth-differentiation factor-7 (GDF7), growth-differentiation factor-8 (GDF8), growth-differentiation factor-9 (GDF9), growth-differentiation factor-10 (GDF10), growth-differentiation factor-11 (GDF11), growth-differentiation factor-15 (GDF15), neurotrophic factor (GDFN), inhibin alpha chain (INHA), inhibin beta A chain (INHBA), inhibin beta B chain (INHBB), inhibin beta C chain (INHBC), inhibin beta E (INHBE), left-right determination factor 1 (LEFTY1), left-right determination factor 2 (LEFTY2), myostatin (MSTN), NODAL, neurturin (NRTN), persephin (PSPN), fibroblast growth factor 1 (FGF1), fibroblast growth factor 2 (FGF2), fibroblast growth factor 3 (FGF3), fibroblast growth factor 4 (FGF4), CBFA1/RUNX2, SRY-box containing gene 9 (SOX9), Interleukin 1 Receptor Antagonist (IL1RA), Interleukin 10 (IL10), Chondroitinase ABC and Neurotrophin-3 (NT3), hepatocyte growth factor (HGF), granulocyte colony-stimulating factor (G-CSF), macrophage colony-stimulating factor (M-CSF), interleukin 6 (IL6), brain-derived neurotropic factor (BDNF), neurotrophin-4 (NT-4), nerve growth factor (NGF), insulin-like growth factor 1 (IGF-1), insulin-like growth factor-2 (IGF-2), fibroblast growth factor 21 (FGF21), human growth hormone (HGH), and combinations thereof.

7. The method of claim 5, wherein the microparticle comprises a core selected from the group consisting of polymers, ceramics, metals, glass and combinations thereof.

8. The method of claim 7, wherein the core comprises one or more of beta-tricalcium phosphate (beta-TCP, β-TCP) and hydroxyapatite (HAP).

9. The method of claim 5, wherein the polynucleotide is in the form of a polynucleotide complex.

10. The method of claim 5, wherein the polynucleotide is selected from the group consisting of messenger RNA (mRNA) and plasmid DNA (pDNA).

* * * * *